United States Patent [19]

Stoss et al.

[11] Patent Number: 4,806,542

[45] Date of Patent: Feb. 21, 1989

[54] ISOHEXIDE PYRIMIDINES TRIAZINES, TRIAZOLES AND IMIDAZOLES USEFUL AS CYTOSTATIC

[75] Inventors: Peter Stoss; Elmar Kaes, both of Illertissen, Fed. Rep. of Germany

[73] Assignee: Heinrich Mack Nachf., Illertissen, Fed. Rep. of Germany

[21] Appl. No.: 19,110

[22] Filed: Feb. 26, 1987

[30] Foreign Application Priority Data

Feb. 28, 1986 [DE] Fed. Rep. of Germany ....... 3606634

[51] Int. Cl.⁴ .................. A61K 31/495; A61K 31/53; C07D 405/14
[52] U.S. Cl. .................................. 514/274; 514/241; 514/272; 514/383; 514/397; 544/232; 544/310; 544/313; 544/317; 544/320; 544/321; 548/262; 548/268; 548/269; 548/336; 548/119
[58] Field of Search ............... 544/310, 232, 214, 222, 544/313, 317, 320, 321, ; 514/274, 241, 272, 383, 397; 548/262, 268, 269, 336, 119

[56] References Cited

PUBLICATIONS

Cope et al., JACS 78, 3177 (1956).
P. M. Kochergin et al., CA 54;8647i (1960).
Goldberg, CA 42, 5564d (1948).

*Primary Examiner*—Donald G. Daus
*Assistant Examiner*—Cecilia Shen
*Attorney, Agent, or Firm*—Peter C. Richardson; Lawrence C. Akers; Paul H. Ginsburg

[57] ABSTRACT

Isohexide nucleosides of the formula I

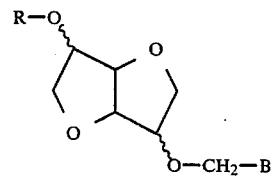

in which R and B have the meaning given in the description, processes for their preparation and their use as medicaments, in particular as cytostatics, virustatics and immunostimulants.

15 Claims, No Drawings

ISOHEXIDE PYRIMIDINES TRIAZINES, TRIAZOLES AND IMIDAZOLES USEFUL AS CYTOSTATIC

BACKGROUND OF THE INVENTION

The present invention relates to novel isohexide nucleosides, processes for their preparation and their use as medicaments, in particular as cytostatics and virustatics.

Isohexides have been known for about 100 years. A number of them have since been recognized as being pharmacologically active. Of these, the coronary pharmaceuticals isosorbide 2,5-dinitrate has been on the market for many years and isosorbide 5-mononitrate recently.

The novel isohexide derivatives according to the invention differ structurally from prior art isohexides by containing a nucleosidic bond with oxygen-containing heterocyclic radicals. The compounds of the invention moreover have different useful pharmacological properties.

SUMMARY OF THE INVENTION

The invention relates to isohexide nucleosides of the formula I:

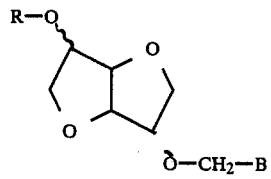

wherein the bond between the ring system and the substituents can be either endocyclic or exocyclic; R is hydrogen; aliphatic acyl having 2 to 5 carbon atoms; aromatic acyl optionally substituted by halogen, lower alkyl or nitro; benzyl, or phosphate; and B is a 5 or 6 membered nitrogen-containing heterocyclic aromatic group such as pyrimidine, triazine, triazole or imidazole. Specifically, B is selected from a) a uracil of the formula:

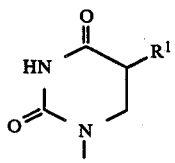

wherein $R^1$ is hydrogen; halogen; alkl, alkenyl or alkynyl having 1 to 6 carbon atoms, optionally substituted by hydroxyl or halogen; (b) a cytosine of the formula:

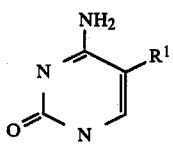

in which $R^1$ has the abovementioned meaning, (c) an isocytosine of the formula:

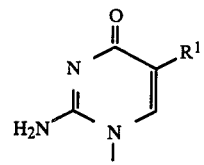

in which $R^1$ has the abovementioned meaning, (d) a 5-azacytosine of the formula:

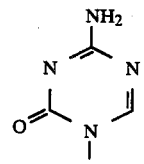

(e) a triazole of the formula:

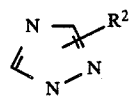

in which the substituent $R^2$ is either in the 3- or 5-position and has the following meaning: hydrogen, carboxyl, alkoxycarbonyl having 1 to 6 carbon atoms, carboxamide, thiocarboxamide or cyano, or (f) an imidazole of the formula:

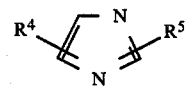

in which $R^4$ and $R^5$ are identical or different and are hydrogen, amino, carboxamide, thiocarboxamide or cyano, or a pharmaceutically acceptable acid addition salt thereof.

The lower alkyl, alkenyl and alkynyl groups in the above definitions contain 1 to 6 carbon atoms and are stright or branched, unless otherwise indicated.

According to a preferred embodiment, the isohexide nucleosides of formula I contain, as R, hydrogen or phosphate and, as B, a uracil of formula II, a cytosine of formula III, an isocytosine of formula IV, $R^1$ in each case representing hydrogen, methyl, ethyl, propyl, isopropyl, butyl, isobutyl, pentyl, hexyl, hydroxymethyl, hydroxyethyl, vinyl, allyl, ethynyl, fluorine, chlorine, bromine, iodine, bromovinyl, iodovinyl or trifluoromethyl, or a 5-azacytosine of formula V, a triazole of formula VI, in which $R^2$ represents carboxamide, methoxycarbonyl or ethoxycarbonyl, or an imidazole of formula VII, in which one of the substituents $R^4$ and $R^5$ is amino and the other is carboxamide or cyano, or a salt thereof with inorganic or organic pharmaceutically acceptable acid.

Isohexides consist of two cis-linked, almost flat tetrahydrofuran rings which form an angle of about 120° with one another. Each of the tetrahydrofuran rings carries a hydroxyl group which may be in the endo or exo position depending on their orientation to the ring system. Four isomeric forms of the compounds of formula I consequently exist, as follows: (1) isomannide nucleosides of formula Ia:

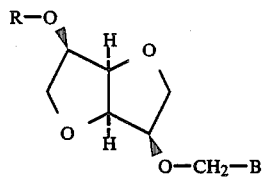

Ia having endo ring substituents in the 2- and 5-positions, R and B having the abovementioned meaning, (2) isoidide nucleosides of the formula Ib:

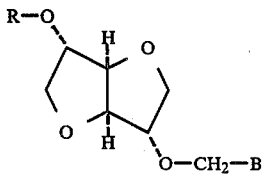

Ib having exo ring substituents in the 2- and 5-positions, R and B having the abovementioned meaning, and (3) isosorbide nucleosides of formulae Ic and Id:

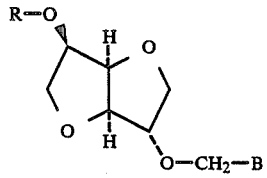  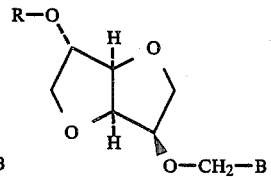

Ic                  Id having one of the two ring substituents in the 2-and 5-positions in each case in the endo-position and the other in the exo-position, R and B having the above-mentioned meaning.

By convention, the exo-position of isosorbides is designated position 2 and the endo-position is designated position 5. Differentiation between positions 2 and 5 is not possible in the case of isomannides and isoidides. A summary of the stereochemistry of isohexides is given by J. A. Mills in Advances in Carbohydrate Chemistry, 10, 1–53 (1965).

The isohexides alternatively are called 1,4:3,6-dianhydro-hexites, 1,4:3,6-dianhydro-hexitols or isohexitols. According to systematic nomenclature, the compounds are bridge ring systems called 2,6-dioxabicyclo[3.3.-0]octane-4,8-diols, or fused systems called hexahydrofuro[3.2-b]furan-3,6-diols. One of the above names may therefore alternatively be used for the compounds according to the invention.

The isohexide nucleosides of formula I may be synthesized by any process suitable for this type of compounds. One such process is for example:

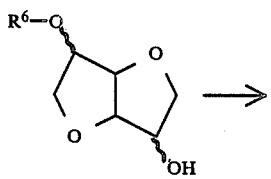

VIII

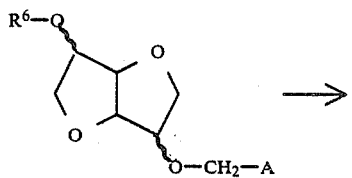

XI

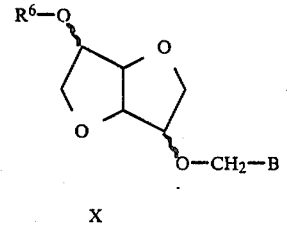

X

According to this equation, compounds (I) are obtained by converting a monosubstituted isohexide of formula VIII in which $R^6$ is a protecting group conventionally used in nucleoside chemistry, in particular, straight or branched aliphatic acyl with 2 to 5 carbon atoms, preferably 2 or 3 carbon atoms, in particular acetyl, or an aromatic acyl, preferably benzoyl optionally substituted by halogen, lower alkyl or nitro, in particular benzoyl, toluyl, chlorobenzoyl or nitrobenzoyl, or benzyl, into a compound of formula IX in which $R^6$ has the abovementioned meaning and A is a leaving group or a leaving atom, and is a halogen, in particular chlorine, bromine or iodine, or acyloxy having a straight or branched aliphatic acyl with 2 to 5 carbon atoms, preferably acetyl.

Such reactions may be carried out in a conventional manner known in the art. If A is halogen, a compound of formula VIII is subjected to halomethylation, which is usually carried out with formaldehyde and hydrogen halide. The formaldehyde may be used either as an aqueous solution or in solid polymeric form. The hydrogen halide may be used either in anhydrous form or in the form of aqueous solutions. A suitable solvent may be used, such as water, methylene chloride, dichloroethane, trichloroethane, chloroform, diethyl ether, diisopropyl ether, tetrahydrofuran, dioxane, benzene, toluene, xylene, or mixtures of the above solvents. The reaction temperatures are between $-50°$ and $+50°$ C., preferably between $-10°$ C. and room temperature. The reaction times are between 0.1 to 24 hours. Certain halomethyl compounds can of course be converted into oteer halomethyl compounds. For example, the chloromethyl compounds may be converted into bromomethyl and iodomethyl compounds by known methods.

Compounds of formula IX in which A is acyloxy can be obtained in a conventional manner from the corresponding halomethyl derivatives by reaction with alkali metal acylates. The alkali metal acylates are advantageously sodium or potassium acylates, preferably sodium acetate or potassium acetate, Solvents are usually employed. Examples of suitable solvents are dimethylformamide, dimethylacetamide, dimethyl sulfoxide, hexamethylphosphoric acid triamide, sulfolane, tetrahydrofuran, dioxane, acetonitrile and acetone.

Reaction temperatures are usually between $-50°$ and $50°$ C., preferably between $-10°$ C. and room temperature, and reaction times are generally between 1 to 24 hours.

The starting compounds of formula VIII are known in most cases or may be prepared by known methods. The compounds of formula IX are novel intermediates. The following are examples of these novel intermediates: 5-0-acetyl-2-0-chloromethyl-isosorbide, 2-0-acetyl-5-0-chloromethyl-isosorbide, 5-0-acetyl-2-0-chloromethyl-isomannide, 5-0-acetyl-2-0-chloromethyl-isoidide, 5-0-benzoyl-2-0-chloromethyl-isosorbide, 2-0-benzoyl-5-0-chloromethyl-isosorbide, 5-0-benzoyl-2-0-chloromethyl-isomannide, 5-0-benzoyl-2-0-chloromethyl-isoidide, 5-0-(4-chlorobenzoyl)-2-0-chloromethyl-isosorbide, 2-0-(4-chlorobenzoyl)-5-0-chloromethyl-isosorbide, 5-0-(4-chlorobenzoyl)-2-0-chloromethyl-isomannide, 5-0-(4-chlorobenzoyl)-2-0-chloromethyl-isoidide, 2-0-chloromethyl-5-0-(4-toluyl)-isosorbide, 5-0-chloromethyl-2-0-(4-toluyl)-isosorbide, 2-0-chloromethyl-5-0-(4-toluyl)-isomannide, 2-0-chloromethyl-5-0-(4-toluyl)-isoidide, 2-0-chloromethyl-5-0(2-nitrobenzoyl)-isosorbide, 5-0-Chloromethyl-2-0-(2-nitrobenzoyl)-isosorbide, 2-0-chloromethyl-5-0(2-nitrobenzoyl)-isomannide, 2-0-chloromethyl-5-0(2-nitrobenzoyl)-isomannide, 2-0-chloromethyl-5-0(2-nitrobenzoyl)-isoidide, 2-0-benzyl-5-0-chloromethyl-isosorbide, 5-0-benzyl-2-0-chloromethyl-isosorbide, 5-0-benzyl-2-0-chloromethyl-isomannide, 5-0-benzyl-2-0-chloromethyl-isoidide, 2-0-acetoxymethyl-5-0-acetyl-isosorbide, 5-0-acetoxymethyl-2-0-acetyl-isosorbide, 2-0-acetoxymethyl-5-0-acetyl-isomannide, 2-0-acetoxymethyl-5-0-acetyl-isoidide, 2-0-acetoxymethyl-5-0-benzoyl-isosorbide, 5-0-acetoxymethyl-2-0-benzoyl-isosorbide, 2-0-acetoxymethyl-5-0-benzoyl-isomannide, 2-0-acetoxymethyl-5-0-benzoyl-isoidide, 2-0-acetoxymethyl-5-0-(4-chlorobenzoyl)-isosorbide, 5-0-acetoxymethyl-2-0-(4-chlorobenzoyl)-isosorbide, 2-0-acetoxymethyl-5-0-(4-chlorobenzoyl)-isomannide, 2-0-acetoxymethyl-5-0-(4-chlorobenzoyl)isoidide, 2-0-acetoxymethyl-5-0-(4-toluyl)-isosorbide, 5-0-acetoxymethyl-2-0-(4-toluyl)-isosorbide, 2-0-acetoxymethyl-5-0-(4-toluyl)-isomannide, 2-0-acetoxymethyl-5-0-(4-toluyl)-isoidide, 2-0-acetoxymethyl-5-0(2-nitrobenzoyl)-isosorbide, 5-0-acetoxymethyl-2-0(2-nitrobenzoyl)-isosorbide, 2-0-acetoxymethyl-5-0(2-nitrobenzoyl)-isomannide, 2-0-acetoxymethyl-5-0(2-nitrobenzoyl)-isoidide, 2-0-acetoxymethyl-5-0-benzyl-isosorbide, 5-0-acetoxymethyl-2-0-benzyl-isosorbide, 2-0-acetoxymethyl-5-0-benzyl-isomannide and 2-0-acetoxymethyl-5-0-benzyl-isoidide.

The compounds of formula IX in which $R^6$ and A have the above meaning are converted in a conventional manner into compounds of formula X in which $R^6$ and B have the above meaning, either by reaction with a nitrogen-containing heterocyclic base of formula XI:

B - H                                                                      XI in which B has the abovementioned meaning, or by reaction with protected derivatives of the above nitrogen-containing heterocyclic base (XI). Such derivatives may be obtained by reaction of a base of formula XI either with compounds containing protective groups customary in nucleoside chemistry, such as aliphatic or aromatic acyl, in particular acetyl or benzoyl, with silylated derivatives of a nitrogen-containing heterocyclic base (XI). The silylated derivatives are obtained by reaction of a base of formula XI with a trialkylsilyl halide, in particular trimethylsilyl chloride, or with a hexaalkyldisilazane, in particular hexamethyl-disilazane, or with mixtures of the two. Such silylated derivatives may be prepared by methods with which the skilled person is familiar. They are in this case without exception known compounds. The silylated derivatives may also be prepared by reacting said trialkylsilyl halide with metal salts of a nitrogen-containing heterocyclic base (XI). The metal salts used are metal salts, preferably silver or mercury salts. The metal salts of a base (XI) may be either employed as such or advantageously formed in situ by adding stoichiometric or catalytic amounts of corresponding metal salts of inorganic or organic acids, such as silver carbonate, silver oxide, mercury chloride, mercury acetate, mercury bromide or mercury cyanide, or by reacting the above trialkylsilyl halide with alkoxy derivatives of a nitrogen-containing heterocyclic base (XI), "alkoxy" being understood as a lower alkoxy group of 1 to 6 carbon atoms, in particular, methoxy or ethoxy.

The above reactions may be carried out either with stoichiometric amounts or with an excess of one reactant, and, if appropriate, in the presence of a solvent suitable for the reaction. Examples of solvents are methylene chloride, dichloromethane, dichloroethane, chloroform, trichloroethane, acetonitrile, dioxane, tetrahydrofuran, dimethylformamide, sulfolane, benzene, toluene, xylene, chlorobenzene, carbon disulfide, carbon tetrachloride and nitromethane. The reaction with the silylated bases may be carried out in the presence of a Lewis acid. Examples of suitable Lewis acids are silicon tetrachloride, tin tetrachloride, titanium tetrachloride, zinc chloride and boron trifluoride. It may be advantageous to add a tertiary amine with the free heterocyclic base. Suitable tertiary amines are tri-lower alkylamines, such as trimethylamine, triethylamine and triisopropylamine, Hunig base or unsubstituted and substituted heterocyclic amines, such as pyridine, 4-dimethylamino-pyridine, or quinoline. The reaction times and reaction temperatures are chosen according to the particular method and may vary within wide limits.

In general, any method which allows linkage of nucleoside bonds can be used for the conversion of IX into X. Sufficient methods and variants of this type are available in the art and are known to the skilled person. For example, some of these processes are mentioned in the literature under the following names: Hilbert-Johnson reaction, Koenigs-Knorr synthesis, silylation process, Friedel-Crafts catalysed silyl method, and melt process.

Some of the compounds of formula X obtained in this manner, in which $R^6$ and B have the meaning given, are compounds of formula I, in particular those in which R is as defined above except hydrogen and phosphate.

A compound (X) may be converted into a compound (I) and, if appropriate, into acid addition salts thereof with pharmaceutically acceptable inorganic or organic acids.

Where R in formula I is hydrogen, the above conversion is carried out by splitting off protective group $R^6$. If $R^6$ is aliphatic or aromatic acyl, removal of $R^6$ is by methods known in nucleoside protective group chemistry, such as transesterification with ammonia/methanol, sodium methylate or potassium methylate/methanol, or basic ion exchanger/methanol. If $R^6$ is benzyl, the benzyl may be removed by known methods, for example catalytic hydrogenation, catalysed transfer hydrogenation, or treatment with boron tribromide or trimethylsilyl iodide.

Compounds of formula I in which R is phosphate may be prepared in a conventional manner by reacting compounds of formula I in which R is hydrogen with a conventional phosphorylating reagent, such as phosphorus oxytrichloride.

The acid addition salts of the invention are formed with inorganic or organic, pharmaceutically acceptable acids. Examples of such salts are hydrochlorides, hydrobromides, nitrates, sulfates, phosphates, acetates, oxalates, fumarates, malates, maleates, malonates, tartrates, lactates, citrates, salicylates, methanesulfonates, benzenesulfonates, toluenesulfonates and naphthalenesulfonates.

These and other salts, such as picrates, of compound (I) may be used for purification of the free bases by converting the free base into a salt, separating the salt, for instance by recrystallization, and liberating the base from the purified salt.

The compounds of formula I are distinguished by a pharmacological action profile unlike that of known isohexides. They have cytostatic, antiviral, enzyme-inhibiting and immunostimulating properties, and low toxicity. They can therefore be used, inter alia, as cytostatics, virustatics and immunostimulants. The present invention also relates to the use of the compounds of formula I in the prevention and treatment of viral diseases and elimination of disturbances in the immune system.

The compounds of formula I may be administered in the usual manner. Suitable presentation forms include oral, rectal, nasal, topical (including buccal, sublingual and ophthalmological), vaginal, parenteral (including subcutaneous, intramuscular, intravenous, intradermal, intrathecal and epidural) and transdermal administrations.

Such pharmaceutical compositions contain a compound (I) according to the invention in an amount of 0.1 to 99.9%. The dosage depends on the intended purpose, the mode of administration, the severity of the illness and the evaluation of the treating physician. The dosage is usally from 0.1 to 300 mg, once or several times daily per kg of body weight, preferably 1 to 50 mg per kg of body weight. A single dose or multiple doses may be administered. In practice, unit doses of 1 to 250 mg once or several times daily are appropriate.

Suitable pharmaceutical formulations are those with which the expert is familiar for the abovementioned administration, such as powders, granules, tablets, capsules, suppositories, suspensions, liquids, injectable preparations and transdermal systems. Solid, semi-solid or liquid excipients or diluents can be used to prepare these pharmaceutical presentation forms. These excipients and diluents inclue correctants, binders, lubricants, emulsifiers. Examples of such agents are starch, such as potato starch and cereal starch, sugars, such as lactose, sucrose, glucose, mannitol and sorbitol, cellulose such as crystalline cellulose, methyl-cellulose, calcium carboxymethyl-cellulose, sodium carboxymethyl-cellulose and hydroxypropyl-cellulose, inorganic materials such as potassium phosphate, calcium sulfate, calcium carbonate and talc, gelatin, gum arabic, polyvinylpyrrolidone, surface-active substances such as fatty acid glycerides and fatty acid sorbitan esters, fatty acid esters of sucrose, polyglycerol and others.

Examples of pharmaceutical formulations using the compounds of formula I are shown below:

| Tablets: | |
| --- | --- |
| Compound I of the invention | 100 mg |
| Lactose | 200 mg |
| Starch | 50 mg |
| Polyvinylpyrrolidone | 5 mg |
| Magnesium stearate | 4 mg |
| Ointment: | |
| Compound I | 0.5 g |
| Glycerol | 15.0 g |
| Macrogol 300 | 20.0 g |
| Polyethylene glycol 1500 | 64.5 g |

The following examples serve to illustrate the invention.

The abbreviations in the examples have the following meanings:
MW = molecular weight
m.p. = melting point
decomp. = decomposition
$[a]_D^{20}$ = optical rotation at 20° C., sodium D line.

The optical rotation values are followed, in parentheses, by the concentration of the solutions measured (for example c=1 means 1 g/100 ml of solution) and the particular solvent.

EXAMPLE 1

2-0-(Uracil-1-yl-methyl)-isosorbide

A. 2-0-Chloromethyl-5-0-(4-toluyl)-isosorbide

A suspension of 66 g of 5-0-(4-toluyl)-isosorbide and 15 g paraformaldehyde in 120 ml methylene chloride was saturated with hydrogen chloride at 0° C. with cooling. A solution was obtained. The solution was left at 0° to 5° C. for 15–20 hours, the water which separated was removed and the solution dried over calcium chloride. After filtration and concentration, an oil was obtained which crystallized when triturated. Crude yield 85 g. Recrystallization from methylene chloride/n-hexane gave an analytically pure product of m.p. 85°–87° C.; $[a]_D^{20}$ +63 (c=2, methylene chloride). $C_{15}H_{17}ClO_5$ MW 312.76

B. 2-0-(Uracil-1-yl-methyl)-5-0-(4-toluyl)-isosorbide 12.8 g of 2,4-bis-(trimethylsilyl)-uracil (prepared by boiling uracil with excess hexamethyldisilazane until the evolution of ammonia had ended and subsequent distillation in vacuo) and 16 g of crude 2-0-chloromethyl-5-0-(4-toluyl)-isosorbide were dissolved in 50 ml anhydrous chloroform. The solution was stirred at room temperature until complete reaction according to thin layer chromatogram (about 2 hours). The reaction mixture was concentrated in vacuo and the syrupy residue dissolved in 100 ml of methylene chloride. 100 ml of saturated aqueous sodium bicarbonate solution was added and the mixture stirred vigorously until the evolution of gas had ended. The organic phase was separated, washed with water and dried over magnesium sulfate. Filtration and concentration of the filtrate gave a syrup which, when recrystallized for 50 ml of methanol, produced 12.7 g product of m.p. 134° C.; $[a]_D^{20}$+59.8 (c=2, methylene chloride). $C_{19}H_{20}N_2O_7$ MW 388.39

C. 2-0-(Uracil-1-yl-methyl)-isosorbide 11.65 g of 2-0-(uracil-1-yl-methyl)-5-0-(4-toluyl)-isosorbide was suspended in 160 ml methanol. 9 ml of 30% methanolic sodium methylate solution was added and the mixture stirred at room temperature until a thin layer chromatogram indicated complete reaction (about 2 hours). The solution was now neutralized by addition of 90 ml of Amberlite IR-120 (H+, methanol-washed), the ion exchanger was filtered with suction and the filtrate concentrated in vacuo. The residue was dissolved in 50 ml methanol under heat. On cooling the solution, crystals were obtained; they were filtered with suction, washed with methanol and ether, and dried in vacuo.

Yield: 6.1 g; m.p. 161° C.; [a]$D^{20}$+41 (c=1, water). $C_{11}H_{14}N_2O_6$ MW 270.25

EXAMPLE 2

2-0-(5-Fluorouracil-1-yl-methyl)-isosorbide

A.

2-0-(5-Fluorouracil-1-yl-methyl)-5-0-(4-toluyl)-isosorbide 13.7 g of 2,4-bis-(trimethylsilyl)-5-fluorouracil (prepared from 5-fluorouracil and hexamethyldisilazane analogous to Example 1B) and 16.4 g of crude 2-0-chloromethyl-5-0-(4-toluyl)-isosorbide (Example 1A) were stirred in 50 ml dry chloroform at room temperature. As soon as a thin layer chromatogram indicated complete reaction (about 4–5 hours), the mixture was concentrated in vacuo, the foam which remained was dissolved in 100 ml methylene chloride and the solution treated with sodium bicarbonate solution and water and dried over magnesium sulfate, as described in Example 1B. After the drying agent had been filtered with suction, the solution was concentrated again in vacuo and 18.3 g of crude product was obtained as a foam. This was further processed without purification. $C_{19}H_{19}FN_2O_7$ MW 406.38

B. 2-0-(5-Fluorouracil-1-yl-methyl)-isosorbide

A mixture of 18.3 g of crude 2-0-(5-fluorouracil-1-yl-methyl)-5-0-(4-toluyl)-isosorbide, 240 ml methanol and 13.5 ml of 30% sodium methylate solution was stirred at room temperature. When the reaction had ended (according to the thin layer chromatogram after about 1 hour), the mixture was neutralized with 135 ml of methanol-moist Amberlite IR-120 (H+) and filtered, and the filtrate was evaporated in vacuo. The vitreous residue was purified by chromatography on silica gel (mobile phase ethyl acetate/methanol 9:1). A foam was obtained, dissolved in water and lyophilized.

Yield: 3 g; m.p. 133°–135° C.; [a]$D^{20}$+38 (c=1, water). $C_{11}F_{13}FN_2O_6$ MW 288.23

EXAMPLE 3

2-0-(5-Bromouracil-1-yl-methyl)-isosorbide

A.

2-0-(5-Bromouracil-1-yl-methyl)-5-0-(4-toluyl)-isosorbide 16.8 g of 2,4-bis-(trimethylsilyl)-5-bromouracil (synthesized in accordance with Example 1B from 5-bromouracil and hexamethyldisilazane) and 16 g of crude 2-0-chloromethyl-5-0-(4-toluyl)-isosorbide (Example 1A) were dissolved in 50 ml dry chloroform. The solution was stirred at room temperature until complete reaction as indicated by a thin layer chromatogram (about 20 hours). After concentration in vacuo, dissolving of the residue in 100 ml methylene chloride, stirring of the solution with sodium bicarbonate solution for one hour and washing with water, a clear solution was obtained which was dried over magnesium sulfate, filtered and concentrated in vacuo. The foam thus obtained (27.8 g) of crude title compound was further reacted without purification. $C_{19}H_{19}BrN_2O^7$ MW 467.30

B. 2-0-(5-Bromouracil-1-yl-methyl)-isosorbide 15 ml of 30% sodium methylate solution was added to 27.8 g of crude 2-0-(5-bromouracil-1-yl-methyl)-5-0-(4-toluyl)-isosorbide and 270 ml methanol and the mixture was stirred at room temperature until a thin layer chromatogram indicated complete transesterification (about 1 hour). The mixture was neutralized with 120 ml of Amberlite IR-120 (H+, methanol-washed), filtered with suction and the filtrate concentrated in vacuo. The syrup which remained was dissolved in 150 ml methanol and the solution cooled to 0° C. After a short time, a precipitate separated. The precipitate was filtered with suction and recrystallized from 95% pure aqueous methanol.

Yield: 17 g; m.p. 169° C.; [a]$D°$+35.5 (c=1, water). $C_{11}H_{13}BrN_2O_6$ MW 349.16

EXAMPLE 4

2-0-(5-Iodouracil-1-yl-methyl)-isosorbide

A.

2-0-(5-Iodouracil-1-yl-methyl)-5-0-(4-toluyl)-isosorbide.

19.1 g of 2,4-bis-(trimethylsilyl)-5-iodouracil (prepared analogous to Example 1B from 5-iodouracil and hexamethyldisilazane) and 16.4 g of 2-0-chloromethyl5-0-(4-toluyl)-isosorbide (Example 1A) were dissolved in 50 ml dry chloroform. The solution was left at room temperature until the reaction was complete (according to the thin layer chromatogram, about 20 hours). All the volatile portions were evaporated in vacuo; the vitreous residue was dissolved in 100 ml acetone, the solution clarified with active charcoal and the resulting solution slowly added dropwise to 1.5 water. The amorphous precipitate formed was filtered with suction, washed with water and dried at 40° in vacuo. Yield: 23.8 g of crude product, which was used in this form in the next stage. $C_{19}H_{19}IN_2O_7$ MW 514.29

B. 2-0-(5-Iodouracil-1-yl-methyl)-isosorbide 15.4 g of 2-0-(5-iodouracil-1-yl-methyl)-5-0-(4-toluyl)-isosorbide in 160 ml of methanol was stirred with 9 ml of 30% sodium methylate solution until a thin layer chromatogram indicated complete reaction (about 2 hours). After neutralization with 90 ml methanol-washed Amberlite IR-120 (H+), the exchanger was filtered with suction, the filtrate evaporated in vacuo and the semi-solid residue stirred with methanol and ether. The solid was filtered with suction and recrystallized from methanol with active charcoal.

Yield: 5.9 g; m.p. 148°–149° C.; [a]$D^{20}$ +30 (c=1, water). $C_{11}H_{13}IN_2O_6$ MW 396.15

EXAMPLE 5

2-0-(5-Methyluracil-1-yl-methyl)-isosorbide

Method 1

13.5 g of 2,4-bis-(trimethylsilyl)-5-methyluracil (preparation from 5-methyluracil and hexamethyldisilazane analogous to Example 1B) was dissolved in 50 ml dry chloroform, and 16.5 g of crude 2-0-chloromethyl-50-(4-toluyl)-isosorbide (Example 1A) was added. The mixture was stirred until a clear solution was obtained and was left until the reaction was complete (about 4 hours according to the thin layer chromatogram). Thereafter, it was concentrated in vacuo, the syrup of crude 2-0-(5-methyluracil-1-yl-methyl)-5-0-(4-toluyl)-isosorbide dissolved in 100 ml methanol, the solution concentrated again and the residue dissolved in 275 ml methanol. After addition of 15 ml of 30% sodium methylate solution, the mixture was stirred at room temperature until, according to the thin layer chromatogram, the transesterification was complete (about 2 hours). The mixture was neutralized in customary manner by addition of 120 ml of Amberlite IR-120 (H+, methanol-moist), filtered, and the filtrate concentrated in vacuo. The oily product was stirred with diethyl ether, decanted, and the syrupy residue dissolved in 30 ml warm ethanol. The solution was cooled gradually to 0° C. and the precipitate which separated was filtered with suction and recrystallized from methanol.

Yield: 6 g; m.p. 132°–133° C.; $[a]D^{20}+39$ (c=1, water). $C_{12}H_{16}N_2OH_6$ MW 284.27

Method 2

A. 2-0-Chloromethyl-5-0-(2-nitrobenzoyl)-isosorbide 100 g of 5-0-(2-nitrobenzoyl)-isosorbide and 20.4 g paraformaldehyde were suspended in 200 ml methylene chloride. Hydrogen chloride was passed in at 0° C. until the suspension was saturated. After the mixture had been left at 0° to 2° C. for four days, the water which separated was removed and the organic phase dried over calcium chloride and concentrated in vacuo. The syrupy crude product was further processed in this form. Yield: 125 g. $C_{14}H_{14}ClNO_7$ MW 343.73

B. 2-0-(5-Methyluracil-1-yl-methyl)-5-0-(2-nitrobenzoyl)-isosorbide.

13.5 g of 2,4-bis-(trimethylsilyl)-5-methyluracil (prepared analogous to Example 1B from 5-methyluracil) and 19 g of crude 2-0-chloromethyl-5-0-(2-nitrobenzoyl)-isosorbide were stirred in 50 ml anhydrous chloroform at room temperature until a thin layer chromatogram revealed complete reaction (5 hours). After all the volatile portions had been distilled in vacuo, the residue was dissolved in 100 ml methylene chloride, and the solution stirred with 100 ml of saturated sodium bicarbonate solution for 1–2 hours. The organic phase was separated, dried over magnesium sulfate, filtered and evaporated, and the residue was recrystallized from ethanol.

Yield: 17 g; m.p. 169°–170° C.; $[a]D^{20}+30.3$ (c=2, methylene chloride). $C_{19}H_{19}N_3O_9$ MW 433.39

C. 2-0-(5-Methyluracil-1-yl-methyl)-isosorbide 15 g of 2-0-(5-methyluracil-1-yl-methyl)-5-0-(2-nitrobenzoyl)-isosorbide, suspended in 150 ml of methanol, was reacted with 10 ml of 30% sodium methylate solution in the customary manner (duration of 1 hour according to the thin layer chromatogram). After neutralization with 100 ml of Amberlite IR-120 (H+, methanol-washed) and filtration, the filtrate was evaporated in vacuo and the semi-solid residue recrystallized from methanol.

Yield: 5.5 g; physical data identical to those of the product prepared by method 1.

Method 3.

A. 5-0-(4-Chlorobenzoyl)-isosorbide 270 g of 4-chlorobenzoyl chloride was added dropwise to a solution of 146 g isosorbide in 1 L pyridine at 15°–20° C. with cooling. Stirring was then continued at 20°–25° C. until, according to the thin layer chromatogram, the reaction had ended. The volatile constituents of the mixture were evaporated in vacuo, the residue was taken up in 1 L methylene chloride and this solution extracted by shaking in succession with in each case 1 L of 2N sulfuric acid, saturated sodium bicarbonate solution and water. Drying over magnesium sulfate, filtration and concentration in vacuo gave a solid residue, which was stirred with ether and filtered with suction. The crude product was purified by recrystallization from toluene.

Yield: 70 g; m.p. 155°–156° C.; $[a]D^{20}+34.5$ (c=1, methylene chloride). $C_{13}H_{13}ClO_5$ MW 284.70

B. 5-0-(4-Chlorobenzoyl)-2-0-chloromethyl-isosorbide

A suspension of 68.4 g of 5-0-(4-chlorobenzoyl)-isosorbide and 15.2 g paraformaldehyde in 150 ml methylene chloride was saturated with hydrogen chloride at 0°. A solution was obtained. The solution was left at 0° to 2° C. for 15–20 hours, the water which separated was removed, the mixture dried over calcium chloride and, after filtration, the filtrate concentrated in vacuo. The syrupy crude product crystallized on tituration. Yield: 78.8 g. The compound was obtained in pure form by recrystallization from methylene chloride/n-hexane, m.p. 66°–69° C.; $[a]D^{20}+35$ (c =2, methylene chloride). $C_{14}H_{14}Cl_2O_5$ MW 333.18

C. 5-0-(4-Chlorobenzoyl)-2-0-(5-methyluracil-1-yl-methyl)-isosorbide 19.8 g of 2,4-bis-(trimethylsilyl)-5-methyluracil (preparation from 5-methyluracil analogous to Example 1B) and 24.5 g of crude 5-0-(4-chlorobenzoyl)-2-0-chloromethyl-isosorbide were dissolved in 100 ml chloroform. The solution was left at room temperature until the reaction was complete (thin layer chromatography check, 18 hours). The solution was treated as described in method 2B and the foamy crude product was purified by chromatography on silica gel (mobile phase chloroform/methanol 9:1). The reaction product was obtained as a white amorphous substance.

Yield: 22.4 g; m.p. 75°–80° C.; $[a]D^{20}+51$ (c=2, methylene chloride). $C_{19}H_{19}ClN_2O_7$ MW 422.83

D. 2-0-(5-Methyluracil-1-yl-methyl)-isosorbide 11.2 g of 5-0-(4-chlorobenzoyl)-2-0-(5-methyluracil-1-yl-methyl)-isosorbide and 10 ml of 30% sodium methylate solution were stirred in 100 ml methanol for 1 hour and the mixture was worked up as described in method 2C. After recrystallization from methanol, 5.6 g product was isolated; the physical data were identical to those obtained for the substance of method 1.

EXAMPLE 6

2-0-(5-Ethyluracil-1-yl-methyl)-isosorbide

A.
2-0-(5-Ethyluracil-1-yl-methyl)-5-0-(4-toluyl)isosorbide 14.2 g of 2,4-bis-(trimethylsilyl)-5-ethyluracil (synthesized from 5-ethyluracil according to Example 1B) and 15.6 g of crude 2-0-chloromethyl-5-0-(4-toluyl)-isosorbide (Example 1A) were dissolved in 50 ml dry chloroform and the solution was allowed to react at room temperature. After 3.5 hours, a thin layer chromatogram indicated complete reaction. The mixture was concentrated in vacuo, the foam which remained was dissolved in 100 ml methylene chloride and the solution was stirred vigorously with 100 ml of saturated sodium bicarbonate solution for 60 minutes. The organic phase was separated, rinsed with water and dried over magnesium sulfate and, after filtration, the filtrate was concentrated in vacuo. The vitreous residue was dissolved in methanol and the solution was left at room temperature for several hours; crystallization occurred. The crystals were filtered with suction and rinsed with methanol.

Yield: 13.45 g; m.p. 134° C.; $[a]D^{20}+68$ (c=2, methylene chloride). $C_2H_{24}N_2O_7$ MW 416.44

B. 2-0-(5-Ethyluracil-1-yl-methyl)-isosorbide 12.5 g of 2-0-(5-ethyluracil-1-yl-methyl)-5-0-(4-toluyl)-isosorbide was dissolved in 160 ml methanol and, and after addition of 9 ml of 30% sodium methylate solution, the mixture was stirred at room temperature until a thin layer chromatogram indicated that the toluyl group had been completely split off (2 hours). The mixture was neutralized in the customary manner with 70 ml of methanol-washed Amberlite IR-120 (H+) and filtered, and the filtrate was concentrated in vacuo. The oily residue was dissolved in 50 ml water and the solution was extracted several times with ether until a thin layer chromatogram indicated the absence of methyl 4-toluylate. A further 50 ml of water was added, the solution was subjected to freeze-drying, and 6 g product obtained, m.p. 48°-60° C.; $[a]D^{20}+38$ (c=1, water). $C_{13}H_{18}N_2O_6$. 0.5 $H_2O$ MW 307.31

EXAMPLE 7

2-0-(5-Isobutyluracil-1-yl-methyl)-isosorbide

A.
2-0-(5-Isobutyluracil-1-yl-methyl)-5-0-(4-toluyl)-isosorbide 15.6 g of crude 2,4-bis-(trimethylsilyl)-5-isobutyluracil (prepared by boiling 8.4 g of 5-isobutyluracil with excess hexamethyldisilazane with the addition of catalytic amounts of ammonium sulfate until the evolution of ammonia had ended, distilling the excess hexamethyldisilazane and degassing the mixture at 90° C. in vacuo for 1-2 hours) and 16.5 g of crude 2-0-chloromethyl-5-0-(4-toluyl)-isosorbide (Example 1A) were dissolved in 50 ml anhydrous chloroform and the solution was left to react at room temperature until, according to the thin layer chromatogram, everything had reacted (about 20 hours). All the volatile portions were now distilled in vacuo, the syrupy residue was taken up in 100 ml of saturated sodium bicarbonate solution until no further carbon dioxide evolved. The organic phase was separated, washed with water and concentrated in vacuo. The vitreous residue was recrystallized from 70% aqueous methanol.

Yield: 17.3 g; m.p. 169°-170° C.; $[a]D^{20}+45.3$ (c=2, methylene chloride). $C_{23}H_{28}N_2O_7$ MW 444.49

B. 2-0-(5-Isobutyluracil-1-yl-methyl)-isosorbide 15 g of 2-0-(isobutyluracil-1-yl-methyl)-5-0(4-toluyl)-isosorbide was suspended in 125 ml methanol. After addition of 10 ml of 30% sodium methylate solution, the mixture was stirred at room temperature until complete esterification was determined by a thin layer chromatogram (1 hour). 80 ml of Amberlite IR-120 (H+, methanol-washed) was added, the mixture stirred until moist indicator paper indicated a neutral reaction, the exchanger filtered and the filtrate concentrated in vacuo to a large degree. The oily residue was stirred thoroughly with diethyl ether, this was decanted and the product purified on a column (silica gel, mobile phase chloroform/methanol 9:1). The fractions containing the desired compound were evaporated, the residue was taken up in water and the mixture was freeze-dried. 6 g of an amorphous powder was obtained; m.p. 53°-62° C.; $[a]D^{20}+34.5$ (c=1, water). $C_{15}H_{22}N_2O_6$. 0.25 $H_2O$ MW 330.86

EXAMPLE 8

2-0-(5-n-Hexyluracil-1-yl-methyl)-isosorbide

A.
2-0-(5-n-Hexyluracil-1-yl-methyl)-5-0-(4-toluyl)-isosorbide 17 g of crude 2,4-bis-(trimethylsilyl)-5-n-hexyluracil (synthesized analogous to Example 7A from 9.8 g of 5-n-hexyluracil) was dissolved in 50 ml dry chloroform, and 16.5 g of crude 2-0-chloromethyl-5-0(4-toluyl)-isosorbide (Example 1A) was added. The end of the reaction was detected by thin layer chromatography (about 1 hour). The mixture was concentrated in vacuo and the vitreous residue dissolved in diethyl ether. After the solution had been left to stand in a refrigerator overnight, the product which precipitated was filtered with suction and washed with diethyl ether.

Yield: 19 g; m.p. 104°-106° C.; $[a]D^{20}+48$ (c=2, methylene chloride). $C_{25}H_{32}N_2O_7$ MW 472.55

B. 2-0-(5-n-Hexyluracil-1-yl-methyl)-isosorbide 18.5 g of 2-0-(5-n-hexyluracil-1-yl-methyl)-5-0(4-toluyl)-isosorbide, 100 ml methanol and 12.5 ml of 30% sodium methylate solution were stirred at room temperature until a thin layer chromatogram indicated complete reaction (1 hour). The mixture was neutralized by addition of 100 ml of Amberlite IR-120 (H+, methanol-washed), the exchanger was filtered and the filtrate concentrated in vacuo. The oily residue was purified by chromatography on silica gel (mobile phase ethyl acetate). Concentration of the corresponding fractions gave 3.5 g of pure title compound as a waxy product; m.p. about 50°-55° C.; $[a]D^{20}+29.5$ (c=2, methylene chloride). $C_{17}H_{26}N_2O_6$. 0.5 $H_2O$ MW 363.42

EXAMPLE 9

2-0-(5-hydroxymethyluracil-1-yl-methyl)-isosorbide

A.
2-0-(5-Hydroxymethyluracil-1-yl-methyl)-5-0-(4-toluyl)-isosorbide 18 g of 2,4-bis-(trimethylsilyl)-hydroxymethyluracil (prepared analogous to Example 1B from 5-hydroxymethyluracil) and 16 g of crude 2-0-chloromethyl-5-0-(4-toluyl)-isosorbide (Example 1A) were dissolved in 50 ml anhydrous chloroform and the solution was left at room temperature until the reaction was complete (2 hours according to the thin layer chromatogram). The mixture was concentrated to a syrup and this was dissolved in 75 ml methanol; crystallization occurred. The crystals were filtered with suction and the crude product was recrystallized from 80% aqueous methanol.

Yield: 13 g; m.p. 192°–193° C. [a]$D^{20}$+49.3 (c=2, dimethylformamide). $C_{20}H_{22}N_2O_8$ MW 418.41

B. 2-0-(5-Hydroxymethyluracil-1-yl-methyl)-isosorbide 16.7 g of 2-0-(5-hydroxymethyluracil-1-yl-methyl)5-0-(4-toluyl)-isosorbide was dissolved in 220 ml methanol, 12 ml of 30% sodium methylate solution was added and the mixture stirred until a thin layer chromatogram indicated complete transesterification (2.5 hours). After neutralization with 120 ml of Amberlite IR-120 (H+, methanol-moist), the mixture was heated to boiling, the exchanger filtered hot with suction and rinsed with 150 ml hot methanol. The combined filtrates were cooled to 0° to 5° C. The solid which precipitated was filtered with suction and recrystallized from 80% aqueous methanol.

Yield: 5.7 g; m.p. 177°–178° C.; [a]$D^{20}$+36.5 (c=1, water). $C_{12}H_{16}N_2O_7$ MW 300.27

EXAMPLE 10

2-0-(5-Trifluoromethyluracil-1-yl-methyl)-isosorbide 16.5 g of crude 2-0-chloromethyl-5-0-(4-toluyl)-isosorbide (Example 1A) was added to 16.2 g of 2,4-bis-(trimethylsilyl)-5-trifluoromethyluracil (preparation analogous to Example 1B from 5-trifluoromethyluracil), dissolved in 50 ml of dried chloroform, and the mixture was allowed to react at room temperature until a complete reaction was determined by a thin layer chromatogram (48 hours). The mixture was concentrated in vacuo, and the vitreous residue was taken up in 100 ml methylene chloride; the formed solution was stirred with 100 ml of saturated sodium bicarbonate solution for 2 hours and the organic layer separated and dried over magnesium sulfate. The organic layer was filtered and evaporated in vacuo and the residue of crude 2-0-(5-trifluoromethyluracil-1-yl-methyl)-5-0-(4-toluyl)-isosorbide was dissolved in 225 ml methanol. After addition of 15 ml of 30% sodium methylate solution, the mixture was stirred at room temperature until, according to the thin layer chromatogram, transesterification was complete; the mixture was neutralized with 200 ml of Amberlite IR-120 (H+, methanol-washed) and filtered, and the filtrate was concentrated in vacuo. The crude substance was purified by chromatography on silica gel (mobile phase ethyl acetate). The fractions containing the desired product were combined and concentrated. The crystalline residue was analytically pure.

Yield: 4.8 g; m.p. 155°–158° C.; [a]$D^{20}$+55 (c=1, methanol). $C_{12}H_{13}F_3N_2O_6$ MW 338.25

EXAMPLE 11

2-0-[E-5-(2-Bromovinyl)-uracil-1-yl-methyl]-isosorbide

A.
2-0-[E-5-(2-Bromovinyl)-uracil-1-yl-methyl]-5-0(4-toluyl)-isosorbide 18.1 g of crude 2,4-bis-(trimethylsilyl)-[E-5-(2-bromovinyl)-uracil](prepared analogous to Example 7A from 10.85 g of E-5-(2-bromovinyl)-uracil) and 16.5 g of crude 2-0-chloromethyl-5-0-(4-toluyl)-isosorbide (Example 1A) were dissolved in 50 ml dry chloroform and the course of the reaction was monitored by layer chromatography. As soon as the reaction was complete (about 7 hours), the solvent was evaporated in vacuo and the syrupy residue stirred with 50 ml of methanol. After some time, crystallization occurred. The crystals were filtered with suction and the crude product was recrystallized from methanol.

Yield: 14 g; m.p. 117°–120° C.; [a]$D^{20}$+42 (c=1, methylene chloride). $C_{21}H_{21}BrN_2O_7$ MW 493.33

B.
2-0-[E-5-(2-Bromovinyl)-uracil-1-yl-methyl]-isosorbide 14 g of 2-0-[E-5-(2-bromovinyl)-uracil-1-ylmethyl]-5-0-(4-toluyl)-isosorbide was dissolved in 200 ml methanol, 9 ml of 30% sodium methylate solution was added and the mixture stirred until the thin layer chromatogram showed that the protective group had been split off completely (1 hour). The mixture was neutralized with 90 ml of methanol-washed Amberlite IR-120 (H+) in the customary manner, the ion exchanger was filtered and the filtrate concentrated in vacuo. The partly crystalline residue was stirred with diethyl ether until everything had becmme powdery, and the powder was then filtered with suction. The crude product was recrystallized from methanol.

Yield: 4.6 g; m.p. 141°–141.5° C.; [a]$D^{20}$+34.5 (c=0.33, water). $C_{13}H_{15}BrN_2O_6$ MW 375.19

EXAMPLE 12

2-0-(Cytosin-1-yl-methyl)-isosorbide

A. 2-0-(Cytosin-1-yl-methyl)-5-0-(4-toluyl)-isosorbide 12.8 g of crude 2,4-bis-(trimethylsilyl)-cytosine (synthesized analogous to Example 7A from 5.6 g of cytosine) was dissolved in 50 ml dry chloroform, and 16 g of crude 2-0-chloromethyl-5-0-(4-toluyl)-isosorbide (Example 1A) was added. As soon as a complete reaction was determined by a thin layer chromatogram (3 hours), the mixture was concentrated in vacuo, the residue dissolved in 100 ml methylene chloride, the solution stirred with 100 ml saturated sodium bicarbonate solution for 1 hour, the organic phase separated and concentrated, and the solid thus obtained stirred with water. The solid was filtered with suction and dried in vacuo at 40°. The crude product was recrystallized from 80% aqueous methanol.

Yield: 8.5 g; m.p. 214°–215° C. (decomp.); [a]$D^{20}$+68.5 (c=2, dimethylformamide). $C_{19}H_{21}N_3O_6$ MW 387.40

B. 2-0-(Cytosin-1-yl-methyl)-isosorbide 12 ml of 30% sodium methylate solution was added to 15.5 g of 2-0-(cytosin-1-yl-methyl)-5-0-(4-toluyl)isosorbide suspended in 220 ml methanol. After transient solution, a precipitate soon separated. After 30 minutes, a thin layer chromatogram indicated complete reaction. The mixture was neutralized by addition of 4 ml of glacial acetic acid, cooled to 0° to 5° C. for 1 hour and filtered with suction, and the residue was washed with ethanol and diethyl ether. The crude product was recrystallized from 80% aqueous methanol.

Yield: 8 g; m.p. 255°–256° C. (decomp.); [a]$D^{20}$+47.5 (c=1, water). $C_{11}H_{15}N_3O_5$ MW 269.26

EXAMPLE 13

2-0-(5-Fluorocytosin-1-yl-methyl)-isosorbide

A.
2-0-(5-Fluorocytosin-1-yl-methyl)-5-0-(4-toluyl)-isosorbide 13.7 g of crude 2,4-bis-(trimethylsilyl)-5-fluorocytosine (prepared from 6.5 g of 5-fluorocytosine analogous to Example 7A) and 16.5 g of crude 2-0-chloromethyl- 5-0-(4-toluyl)-isosorbide (Example 1A) were dissolved in 50 ml dry chloroform. After a short time, a precipitate started to separate. When everything had reacted (after 20 hours according to the thin layer chromatogram), all volatile portions were evaporated in vacuo and the residue was recrystallized from methanol.

Yield: 12.4 g; m.p. 237°-238° C.; $[a]D^{20}+56$ (c=2, dimethylformamide). $C_{19}H_{20}FN_3O_6$ MW 405.39

B. 2-0-(5-Fluorocytosin-1-yl-methyl)-isosorbide 12.15 g of 2-0-(5-fluorocytosin-1-yl-methyl)-5-0-(4-toluyl)-isosorbide and 9 ml of 30% sodium methylate solution were stirred in 165 ml methanol until a thin layer chromatogram indicated complete reaction (45 minutes). The mixture was neutralized with 3 ml glacial acetic acid and the solid which precipitated was filtered with suction and recrystallized from 80% methanol.

Yield: 4.7 g; m.p. 250°-251° C. (decomp.), $[a]D^{20}+39.5$ (c=1, water). $C_{11}H_{14}FN_3O_5$ MW 287.26

The hydrochloride was obtained by dissolving in methanolic hydrochloric acid and precipitating with diethyl ether. m.p. 189° C. (decomp.); $[a]D^{20}+32$ (c=1, water. $C_{11}H_{14}FN_3O_5$ . HCl MW 287.26

EXAMPLE 14

2-0-(5-Chlorocytosin-1-yl-methyl)-isosorbide

A. 5-0-Benzoyl-2-0-chloromethyl-isosorbide 89.5 g of 5-0-benzoyl-isosorbide was dissolved in 165 ml methylene chloride, 21.5 g paraformaldehyde was added and the mixture was saturated with hydrogen chloride at 0° C. The mixture was left at 0° to 20° C. for 18-20 hours, the water of reaction which separated was removed, the methylene chloride solution was dried over calcium chloride and then over magnesium sulfate and filtered, and the filtrate was concentrated in vacuo. The crude product obtained as a viscous oil was reacted further in this form.

Yield: 112 g. $C_{14}H_{15}ClO_5$ MW 298.73

B. 5-0-Benzoyl-2-0-(5-chlorocytosin-1-yl-methyl)-isosorbide 14.5 g of crude 2,4-bis-(trimethylsilyl)-5-chloro-cytosine (prepared analogous to Example 7A from 7.3 g of 5-chlorocytosine) and 16 g of crude 5-0-benzoyl-2-0-chloromethyl-isosorbide were dissolved in 50 ml chloroform (anhydrous) and the solution was stirred at room temperature until the reaction had ended (18 hours). The mixture was evaporated in vacuo, the syrupy residue dissolved in 100 ml methylene chloride, the solution stirred with 100 ml sodium bicarbonate solution for 1 hour and the organic layer separated and concentrated. The crude product was purified by chromatography on silica gel (mobile phase chloroform/methanol 5:1).

Yield: 4.6 g; m.p. 199°-201° C.; $[a]D^{20}+62$ (c=1, methylene chloride). $C_{18}H_{18}ClN_3O_6$ MW 407.82

C. 2-0-(5-Chlorocytosin-1-yl-methyl)-isosorbide 9 g of 5-0-benzoyl-2-0-(5-chlorocytosin-1-yl-methyl)-isosorbide, suspended in 100 ml methanol, was stirred with 4 ml 30% sodium methylate solution at room temperature for 1 hour; a thin layer chromatogram showed that the benzoyl group had been split off completely. The mixture was neutralized by stirring with 40 ml Amberlite IR-120 (H+, methanol-washed) and filtered, and the filtrate concentrated to dryness in vacuo. The residue was recrystallized from ethanol.

Yield: 3.4 g; m.p. 214° C.; $[a]D^{20}+49.5$ (c=1, water). $C_{11}H_{14}ClN_3O_5$ MW 303.71

EXAMPLE 15

2-0-(5-Iodocytosin-1-yl-methyl)-isosorbide

A. 2-0-(5-Iodocytosin-1-yl-methyl)-5-0-(4-toluyl)-isosorbide 19 g of crude 2,4-bis-(trimethylsilyl)-5-iodocytosine (synthesized analogous to Example 7A from 11.85 g of 5-iodocytosine) was dissolved in 50 ml dry chloroform, 16 g of crude 2-0-chloromethyl-5-0-(4-toluyl)-isosorbide (Example 1A) was added and the mixture stirred at room temperature until a thin layer chromatogram indicated complete reaction (2 hours). The mixture was concentrated in vacuo, the vitreous residue dissolved in 100 ml methylene chloride and this solution stirred with 100 ml saturated sodium bicarbonate solution for 1 hour. The organic phase was separated and concentrated in vacuo. The residue was recrystallized from methanol.

Yield: 9.1 g; m.p. 190°-191° C. (decomp.); $[a]D^{20}+42.5$ (c=2, methylene chloride). $C_{19}H_{20}IN_3O_6$ MW 513.30

B. 2-0-(5-Iodocytosin-1-yl-methyl)-isosorbide 10.3 g of 2-0-(5-iodocytosin-1-yl-methyl)-5-0-(4-toluyl)-isosorbide was suspended in 110 ml methanol. 6 ml 30% sodium methylate solution was added dropwise and the mixture stirred until complete reaction as indicated by a thin layer chromatogram (30 minutes). The mixture was neutralized with 2 ml glacial acetic acid and kept at 0° to 5° C. for 1 hour. The crude product which precipitated was filtered with suction and recrystallized from methanol with the addition of active charcoal.

Yield: 4.3 g; m.p. 181° C. (decomp.); $[a]D^{20}+32$ (c=1, water). $C_{11}H_{14}IN_3O_5$ MW 395.17

EXAMPLE 16

2-0-(Isocytosin-1-yl-methyl)-isosorbide

A. 2-0-(Isocytosin-1-yl-methyl)-5-0-(4-toluyl)-isosorbide 12.8 g of crude 2,4-bis-(trimethylsilyl)-isocytosine (prepared analogous to Example 7A from 5.6 g of isocytosine) and 16 g of crude 2-0-chloromethyl-5-0(4-toluyl)-isosorbide (Example 1A), dissolved in 50 ml dry chloroform, was stirred at room temperature until complete reaction was indicated by a thin layer chromatogram (2 hours). The mixture was evaporated in vacuo, the residue dissolved in 100 ml methylene chloride, the solution stirred with 100 ml sodium bicarbonate solution for 1 hour, the organic phase separated and concentrated and the residue recrystallized from methanol.

Yield: 5.2 g; m.p. 223°-225° C. (decomp.); $[a]D^{20}+53.5$ (c=2, dimethylformamide). $C_{19}H_{21}N_3O_6$ MW 387.40

B. 2-0-(Isocytosin-1-yl-methyl)-isosorbide 5.2 g of 2-0-(isocytosin-1-yl-methyl)-5-0-(4-toluyl)-isosorbide and 4 ml 30% sodium methylate solution were stirred in 70 ml methanol until, according to the thin layer chromatogram, splitting off of the toluyl group had ended (1 hour). The mixture was neutralized by addition of 40 ml methanol-washed ion exchanger (Amberlite IR-120, H+), the exchanger filtered, the filtrate evaporated in vacuo and the solid residue recrystallized from ethanol.

Yield: 2.3 g; m.p. 192°–193° C. (decomp.); $[a]_D^{20} +45.5$ (c=1, water). $C_{11}H_{15}N_3O_5$ MW 269.26

EXAMPLE 17

2-0-(5-Methylisocytosin-1-yl-methyl)-isosorbide

A.
2-0-(5-Methylisocytosin-1-yl-methyl)-5-0-(4-toluyl)-isosorbide 27 g of crude 2,4-bis-(trimethylsilyl)-5-methyl isocytosine (prepared analogous to Example 7A from 12.5 g of 5-methylisocytosine) was dissolved in 100 ml dry chloroform, and 33 g of crude 2-0-chloromethyl-5-0-(4-toluyl)-isosorbide (Example 1A) was added. The mixture was stirred until complete reaction as shown by a thin layer chromatogram (15 hours), concentrated in vacuo and the oily residue recrystallized from methanol.

Yield: 18.3 g; m.p. 165°–166° C.; $[a]_D^{20} +56.5$ (c=2, dimethylformamide). $C_{20}H_{23}N_3O_6$ MW 401.43

B. 2-0-(5-Methylisocytosin-1-yl-methyl)-isosorbide 18.3 g of 2-0-(5-methylisocytosin-1-yl-methyl)-5-0-(4-toluyl)-isosorbide, suspended in 200 ml methanol, was stirred with 15 ml of 30% sodium methylate solution at room temperature until everything had dissolved and a thin layer chromatogram indicated complete reaction (1 hour). 150 ml of methanol-washed Amberlite IR-120 (H+) was added, the mixture stirred until the solution had a neutral reaction, the exchanger was filtered with suction and the filtrate evaporated in vacuo. The waxy residue was recrystallized from methanol.

Yield: 6.2 g; m.p. 197°–198° C.; $[a]_D^{20} +42.5$ (c=1, water). $C_{12}H_{17}N_3O_5$ MW 283.29

EXAMPLE 18

2-0-(3-Methoxycarbonyl-1,2,4-triazol-1-yl-methyl)isosorbide isosorbide

A.
2-0-(3-Methoxycarbonyl-1,2,4-triazol-1-yl-methyl)-5-0-(4-toluyl)-isosorbide and
2-0-(5-methoxy-carbonyl-1,2,4-triazol-1-yl-methyl)-5-0-(4-toluyl)-isosorbide 20 g of the crude trimethylsilyl derivative of methyl 1,2,4-triazole-3-carboxylate (prepared analogous to Example 7A from 12.7 g of methyl 1,2,4-triazole-3-carboxylate) and 33 g of crude 2-0-chloromethyl-5-0-(4-toluyl)-isosorbide (Example 1A) were dissolved in 100 ml dry chloroform and the solution was allowed to react at room temperature until, according to the thin layer chromatogram, the reaction had ended (20 hours). The mixture was evaporated in vacuo, the vitreous residue dissolved in 200 ml methylene chloride, the solution stirred with 100 ml of sodium bicarbonate solution for 1 hour and the methylene chloride layer separated, dried over magnesium sulfate and concentrated in vacuo. The residue was purified by chromatography on silica gel (mobile phase chloroform/methanol 9:1), resolution of the two isomers taking place at the same time. 2-0-(3-Methoxycarbonyl-1,2,4-triazol-1-yl-methyl)-5-0-(4-toluyl)-isosorbide was obtained by evaporation of the corresponding fractions.

Yield: 9.9 g; m.p. 138°–139° C.; $[a]_D^{20} +53$ (c=2, methylene chloride). In addition, 7.8 g of 2-0-(5-methoxycarbonyl-1,2,4-triazol-1-yl-methyl)-5-0-(4-toluyl)-isosorbide was isolated; m.p. 110° C.; $[a]_D^{20} +48$ (c=2, methylene chloride). $C_{19}H_{21}N_3O_7$ MW 403.40

B.
2-0-(3-Methoxycarbonyl-1,2,4-triazol-1-yl-methyl)-isosorbide 6 ml of 30% sodium methylate solution was added to 8 g of 2-0-(3-methoxycarbonyl-1,2,4-triazol-1-yl-methyl)-5-0-(4-toluyl)-isosorbide, dissolved in 110 ml methanol, and the mixture was stirred at room temperature until complete reaction was indicated by a thin layer chromatogram (1 hour). The mixture was neutralized by stirring with 60 ml of Amberlite IR-120 (H+, methanol-washed), the exchanger filtered with suction, the filtrate concentrated in vacuo and the oily residue recrystallized from methanol/ether.

Yield: 2.6 g; m.p. 109°–110° C.; $[a]_D^{20} +40.5$ (c=1, water). $C_{11}H_{15}N_3O_6$ MW 285.26

EXAMPLE 19

2-0-(5-Methoxycarbonyl-1,2,4-triazol-1-yl-methyl)-isosorbide 8 g of 2-0-(5-methoxycarbonyl-1,2,4-triazol-1-yl-methyl)-5-0-(4-toluyl)-isosorbide (preparation in Example 18A) was dissolved in 110 ml methanol and the solution stirred with 3 ml of 30% sodium methylate solution until, according to the thin layer chromatogram, the transesterification had ended. The mixture was neutralized by addition of 30 ml of Amberlite IR-120 (H+, methanol-washed), the exchanger filtered, the filtrate concentrated in vacuo to a large degree and the resulting oil stirred with 100 ml diethyl ether; crystallization occurred. The crude product was recrystallized from methanol/diethyl ether.

Yield: 3 g; m.p. 106° C.; $[a]_D^{20} +37.5$ (c=1, water) $C_{11}H_{15}N_3O_6$ MW 285.26

EXAMPLE 20

2-0-(3-Carbamoyl-1,2,4-triazol-1-yl-methyl)-isosorbide

Method 1

8 g of 2-0-(3-methoxycarbonyl-1,2,4-triazol-1-yl-methyl)-5-0-(4-toluyl)-isosorbide was suspended in 60 ml methanol, and 7.5 g ammonia was passed in at 20°–25° C., with cooling resulting in dissolution. After about 22 hours, a precipitate started to separate. After 27–30 hours, the precipitate was filtered with suction and rinsed with methanol and diethyl ether. The crude product was recrystallized from 90% aqueous methanol.

Yield: 3.7 g; m.p. 173° C.; $[a]_D^{20} +38$ (c=1, water). $C_{10}H_{14}N_4O_5$ MW 270.25

Method 2

A. 2-0-Acetoxymethyl-5-0-(4-toluyl)-isosorbide 39 g of 2-0-chloromethyl-5-0-(4-toluyl)-isosorbide was dissolved in 400 ml N,N-dimethylformamide, and 19 g anhydrous sodium acetate added. The mixture was stirred at room temperature for 2 days and concentrated in vacuo, the residue dissolved in 500 ml of methylene chloride, undissolved portions filtered with suction and the filtrate extracted twice with 500 ml water each time. The organic phase was separated and dried over magnesium sulfate. After filtration and evaporation in vacuo, a viscous oil was obtained, which crystallized after some time. The compound was reacted further as the crude substance.

Yield: 36.7 g. An analytically pure product was obtained by recrystallization from methanol/water 2:1. m.p. 61°–64° C.; $[a]_D^{20}+37$ (c=2, methylene chloride). $C_{17}H_{20}O_7$ MW 336.35

B.
2-0-(-Methoxycarbonyl-1,2,4-triazol-1-yl-methyl)-5-0-(4-toluyl)-isosorbide 33.3 g of 2-0-acetoxymethyl-5-0-(4-toluyl)-isosorbide was warmed to 140° C. and 12.5 g of methyl 1,2,4-triazole-3-carboxylate and then 0.27 g of bis-(4-nitrophenyl) phosphate were added to the resulting melt with stirring. A vacuum was applied and the acetic acid formed distilled off. After 1 hour, the mixture was cooled and the vitreous residue recrystallized from methanol. Yield: 8.5 g. The physical data of the product were identical to those of the compound described in Example 18A.

C.
2-0-(3-Carbamoyl-1,2,4-triazol-1-yl-methyl)isosorbide 6.8 g of 2-0-(3-methoxycarbonyl-1,2,4-triazol-1-yl-methyl)-5-0-(4-toluyl)-isosorbide was reacted with methanolic ammonia as described in method 1. Yield: 2.0 g. The data of the compound are identical to those of the substance described in method 1.

EXAMPLE 21
2-0-(5-Carbamoyl-1,2,4-triazol-1-yl-methyl)-isosorbide 9.5 g ammonia was passed into a solution of 10 g of 2-0-(5-methoxycarbonyl-1,2,4-triazol-lyl-methyl)5-0-(4-toluyl)-isosorbide in 75 ml methanol at 20°–25° C. After the mixture had been left at room temperature for two days, a crystalline product separated out and was filtered with suction and recrystallized from 90% aqueous methanol.

Yield: 4.4 g; m.p. 158°–159° C.; $[a]_D^{20}+41$ (c=1, water). $C_{10}H_{14}N_4O_5$ MW 270.25

EXAMPLE 22
2-0-(5-Azacytosin-1-yl-methyl)-isosorbide

A.
2-0-(5-Azacytosin-1-yl-methyl)-5-0-(4-toluyl)isosorbide 25.6 g of crude 2,4-bis-trimethylsilyl)-5-azacytosine (prepared analogous to Example 7A from 11.2 g of 5-azacytosine) was dissolved in 100 ml 1,2-dichloroethane. 33 g of crude 2-0-chloromethyl-5-0-(4-toluyl)-isosorbide and then 8 ml of tin tetrachloride were added. The mixture was stirred at room temperature until, according to the thin layer chromatogram, everything had reacted (3–4 hours) 300 ml of saturated sodium bicarbonate solution was slowly added dropwise. As soon as the evolution of gas had ended, the organic phase was separated, washed with water, dried over magnesium sulfate and concentrated in vacuo. The vitreous residue was purified by chromatography on silica gel (mobile phase chloroform/methanol 3:1).

Yield: 6.4 g; m.p. 212°–213° C.; $[a]_D^{20}+65$ (c=1, methylene chloride). $C_{18}H_{20}N_4O_6$ MW 388.39

B. 2-0-(5-Azacytosin-1-yl-methyl)-isosorbide 6.4 g of 2-0-(5-azacytosin-1-yl-methyl)-5-0(4-toluyl)-isosorbide was suspended in 100 ml methanol, 6 ml of 30% sodium methylate solution was added dropwise and the mixture was stirred at room temperature. After about 20 minutes, there was dissolution, and after a further 5 minutes a solid precipitated. At this point, according to the thin layer chromatogram, the transesterification was complete. The mixture was neutralized by addition of 2.3 ml glacial acetic acid, cooled to 0° C. and filtered with suction. The residue was washed with methanol and dried in vacuo at 40° C.

Yield: 2.8 g; m.p. 195° C.; $[a]_D^{20}+41.8$ (c=2, water). $C_{10}H_{14}N_4O_5$ MW 270.25

EXAMPLE 23
2-0-(5-Amino-4-carbamoyl-imidazol-1-yl-methyl)-isosorbide

A.
2-0-(5-Amino-4-carbamoyl-imidazol-1-yl-methyl)5-0-(4-toluyl)-isosorbide 12.6 g of 5-aminoimidazole-4-carboxamide was dissolved in 750 ml acetonitrile, and 44 ml triethylamine and 62 g of crude 2-0-chloromethyl-5-0-(4-toluyl)-isosorbide were added in succession. The mixture was stirred at room temperature until complete reaction was shown in the thin layer chromatogram (about 3 hours). The triethylammonium chloride was filtered and the filtrate evaporated in vacuo. The residue was dissolved in 400 ml methylene chloride and the solution extracted by shaking with 400 ml water. The title compound was isolated by concentration of the organic phase and recrystallization of the residue from 20% aqueous methanol.

Yield: 5.7 g; m.p. 142°–143° C.; $[a]_D^{20}+34.5$ (c=1, methylene chloride). $C_{19}H_{22}N_4O_6$ MW 402.42

B.
2-0-(5-Amino-5-carbamoyl-imidazol-1-yl-methyl)-isosorbide 7.4 g of 2-0-(5-amino-4-carbamoyl-imidazol-1-yl-methyl)-5-0-(4-toluyl)-isosorbide was dissolved in 200 ml methanol, and 6 ml 30% sodium methylate solution was added. The mixture was stirred until, according to the thin layer chromatogram, everything had reacted (2 hours), neutralized by stirring with 60 ml of Amberlite IR-120 (H+, methanol-washed) and filtered and the filtrate concentrated in vacuo. The residue was recrystallized from isopropanol.

Yield: 2.1 g; m.p. 130°–132° C.; $[a]_D^{20}+36.5$ (c=1, water). $C_{11}H_{16}N_4O_5$ MW 284.28

EXAMPLE 24
5-0-(5-Iodouracil-1-yl-methyl)-isosorbide

Method 1.

A. 2-0-(4-Toluyl)-isosorbide 188 g of 5-0-acetyl-isosorbide was dissolved in a mixture of 500 ml methylene chloride and 160 ml pyridine. 170 g 4-toluyl chloride was added dropwise in the course of about 30 minutes at an internal temperature of 20° C., while cooling with ice. The mixture was stirred at the same temperature until a thin layer chromatogram indicated complete reaction (1–2 hours). The reaction mixture was poured into 2 L of ice-water and subsequently stirred for 30 minutes. The organic phase was separated and washed in succession with saturated sodium bicarbonate solution, cold dilute sulfuric acid, sodium bicarbonate solution again and finally water. After drying over magnesium sulfate, filtration and concentration in vacuo 305 g of 5-0-acetyl-2-0-(4- toluyl)-isosorbide as a non-crystalline waxy product was obtained which was further processed directly:

276 g of the crude product was dissolved in 2.3 L ethanol, 5 ml of 30% sodium methylate solution added and the mixture cooled to 10° C. with stirring. The mixture was stirred at this temperature until, according to the thin layer chromatogram, everything had reacted (2 hours) and neutralized by addition of 2 ml glacial acetic acid. The volatile portions were evaporated in vacuo. The syrup which remained was recrystallized from toluene/petroleum ether.

Yield: 139.5 g; m.p. 74° C.; $[a]D^{20}+65$ (c=2, methylene chloride). $C_{14}H_{16}O_5$ MW 264. 28

B. 5-0-Chloromethyl-2-0-(4-toluyl)-isosorbide 119 g 2-0-(4-toluyl)-isosorbide and 27 g paraformaldehyde were suspended in 220 ml methylene chloride. The suspension was cooled to 0° C. and saturated with hydrogen chloride (duration about 2 hours). The solution thus obtained was left at 0 to 20° C. for 15-20 hours, the water of reaction was separated, the methylene chloride solution dried over calcium chloride and magnesium sulfate and filtered, and the filtrate concentrated in vacuo. The oil which remained crystallized on trituration. The crude product was used without further purification.

Yield: 144 g. The substance was obtained in pure form by recrystallization from methylene chloride/n-hexane, m.p. 100°-102° C.; $[a]D^{20}+157$ (c=2, methylene chloride). $C_{15}H_{17}ClO_5$ MW 312.76

C. 5-0-(5-Iodouracil-1-yl-methyl)-isosorbide 19.1 g of 2,4-bis-(trimethylsilyl)-5-iodouracil (synthesized analogous to Example 1B from 5-iodouracil) and 16.5 g of the crude 5-0-chloromethyl-2-0-(4-toluyl)-isosorbide were dissolved in 50 ml dry chloroform. The solution was allowed to react at room temperature until a thin layer chromatogram indicated complete reaction (18 hours). The mixture was concentrated in vacuo, the residue dissolved in 100 ml methylene chloride. The formed solution was extracted by stirring with 100 ml of saturated sodium bicarbonate solution for 1 hour, separated and dried over magnesium sulfate. Filtration and evaporation of the solvent gave 25.3 g of the crude product 5-0-(iodouracil-1-yl-methyl)-2-0-(4-toluyl)-isosorbide, which was further processed directly:

The crude product was dissolved in 300 ml methanol, 15 ml of 30% sodium methylate solution added and the mixture left at room temperature until complete reaction was shown in the thin layer chromatogram (2 hours). After neutralization with 150 ml of ion exchanger (methanol-washed Amberlite IR-120, H+ form) and filtration, the filtrate was evaporated in vacuo to give a syrup, which slowly crystallized completely. The pure title compound was obtained by recrystallization from water.

Yield: 6.5 g; m.p. 169°-170° C.; $[a]D^{20}+52$ (c=1, water). $C_{11}H_{13}IN_2O_6$ MW 396.15

Method 2.

A. 2-0-Acetyl-5-0-chloromethyl-isosorbide

A suspension of 47 g of 2-0-acetyl-isosorbide and 15 g paraformaldehyde in 120 ml methylene chloride was saturated with hydrogen chloride at 0° C. and the resulting solution left at 0° C. for 15 to 20 hours. The water which separated was removed and the organic phase dried over calcium chloride and concentrated in vacuo. A non-crystallizing oil was obtained. Yield: 59.6 g. The crude compound was reacted further in this form. $C_9H_{13}ClO_5$ MW 236.66

B. 5-0-(5-Iodouracil-1-yl-methyl)-isosorbide 19.1 g of 2,4-bis-(trimethylsilyl)-5-iodouracil (synthesized analogous to Example 1B from 5-iodouracil) and 12.4 g of crude 2-0-acetyl-5-0-chloromethyl-isosorbide were dissolved in 50 ml chloroform. The solution was stirred at room temperature until, according to the thin layer chromatogram, the reaction had ended. Thereafter, the mixture was concentrated in vacuo and the residue taken up in 50 ml methylene chloride. 50 ml methanol and then 20 ml of the ion exchanger Dowex 1×2 (OH−, methanol-washed) were added. The mixture was stirred for 15 minutes, the exchanger filtered and the filtrate concentrated in vacuo. The amorphous crude 2-0-acetyl-5-0-(5-iodouracil-1-yl-methyl)-isosorbide (19.5 g) was dissolved in 200 ml methanol, saturated with ammonia at 0° C. and the solution was left at 0° C. for 24 hours. A thin layer chromatogram indicated complete reaction. All the volatile portions were evaporated in vacuo, the residue was dissolved again in methanol and the solution evaporated again. The vitreous crude product was purified by chromatography on silica gel (mobile phase ethyl acetate), the appropriate fractions were concentrated and the residue recrystalized from water. Yield: 6.6 g; the physical data of the product were identical to those of the compound prepared by method 1.

EXAMPLE 25

5-0-(3-Carbamoyl-1,2,4-triazol-1-yl-methyl)-isosorbide

A.

5-0-(3-Methoxycarbonyl-1,2,4-triazol-1-yl-methyl)2-0-(4-toluyl)-isosorbide and 5-0-(5-methoxycarbonyl-1,2,4-triazol-1-yl-methyl)-2-0-(4-toluyl)-isosorbide 20 g of the crude trimethylsilyl derivative of methyl 1,2,4-triazole-3-carboxylate (prepared analogous to Example 7A from 12.7 g of methyl 1,2,4-triazole-3-carboxylate) together with 34 g of crude 5-0-chloromethyl-2-0-(4-toluyl)-isosorbide (preparation in Example 24, method 1B) were dissolved in 100 ml anhydrous chloroform. The solution was left at room temperature for 18 to 20 hours, until a thin layer chromatogram indicated complete reaction. The mixture was concentrated in vacuo, and the syrupy residue dissolved in 200 ml of methylene chloride. 20 ml methanol and 200 ml of saturated sodium bicarbonate solution were added and the mixture was stirred until the evolution of gas had ceased. The organic layer was separated, dried over magnesium sulfate and evaporated in vacuo. The crude product was purified by column chromatography on silica gel; the isomers were resolved at the same time. 5-0-(3-Methoxycarbonyl-1,2,4-triazol-1-yl-methyl)-2-0-(4-toluyl)-isosorbide was isolated by concentrating the appropriate fractions.

Yield: 16.1 g; m.p. 88°-89° C.; $[a]D^{20}+113$ (c=2, methylene chloride).

8.8 g of oily 5-0-(5-methoxycarbonyl-1,2,4-triazol-1-yl-methyl)-2-0-(4-toluyl)-isosorbide was thereby obtained. $C_{19}H_{21}N_3O_7$ MW 403.40

B.

5-0-(3-Carbamoyl-1,2,4-triazol-1-yl-methyl)-isosorbide 12.1 g of 5-0-(3-methoxycarbonyl-1,2,4-triazol-1-yl-methyl)-2-0-(4-toluyl)-isosorbide was dissolved in 90 ml methanol, and 11.5 g ammonia was passed in at a maximum temperature of 25° C. The mixture was stirred at room temperature for 20 hours and cooled to 0 to 5° C. The precipitate formed was filtered with suction. 7.7 g of crude 5-0-(3-carbamoyl-1,2,4-triazol-1-yl-methyl)-2-0-(4-toluyl)-isosorbide was isolated and further reacted directly.

The compound was suspended in 200 ml methanol, 10 ml of 30% sodium methylate solution added and the mixture stirred at room temperature until transesterification was complete (1 hour according to the thin layer chromatogram). After neutralization with 100 ml of Amberlite IR-120 (H+, methanol-washed), the solvent was evaporated in vacuo, the solid reside stirred with diethyl ether, filtered with suction and the product dried in vacuo. Yield: 4.1 g; m.p. 145°–147° C.; $[a]D^{20}+80$ (c=1, water). $C_{20}H_{14}N_4O_5$ MW 270.25

EXAMPLE 26

5-0-(5-Carbamoyl-1,2,4-triazol-1-yl-methyl)-isosorbide 8.1 g of 5-0-(5-methoxycarbonyl-1,2,4-triazol-1-yl-methyl)-2-0-(4-toluyl)-isosorbide (preparation in Example 25A) was dissolved in 60 ml methanol, and 7.7 g ammonia passed in at 20 to 25° C. After the mixture had been left at room temperature for 4 days, the volatile portions were evaporated in vacuo and the residue was recrystallized from methanol.

Yield: 3.5 g; m.p. 132°–133° C.; $[a]D^{20}+80$ (c=1, water). $C_{10}H_{14}N_4O_5$ MW 270.25

EXAMPLE 27

5-0-(5-Azacytosin-1-1-methyl)-isosorbide

A.

5-0-(5-Azacytosin-1-yl-methyl)-2-0-(4-toluyl)isosorbide 25.6 g of crude 2,4-bis-(trimethylsilyl)-5-azacytosine (prepared analogous to Example 7A from 11.2 go of 5-azacytosine) was dissolved in 300 ml of 1,2-dichloroethane. 8 ml of tin tetrachloride and 33 g of crude 5-0-chloromethyl-2-0-(4-toluyl)-isosorbide (synthesis in Example 24, method 1B) were added. The mixture was stirred until everything had dissolved and was left to stand until complete reaction according to the thin layer chromatogram (18 hours). 300 ml of saturated sodium bicarbonate solution was added dropwise with vigorous stirring, and the mixture stirred until the evolution of gas had ended. The organic phase was separated and concentrated in vacuo. The crude product which remained was purified by chromatography on silica gel (mobile phase chloroform/methanol 9:1). The appropriate fractions were concentrated in vacuo and the residue was recrystallized from isopropanol.

Yield: 5.2 g; m.p. 215°–218° C.; $[a]D^{20}+56$ (c=0.5, methylene chloride). $C_{18}H_{20}N_4O_6$ MW 388.39

B. 5-0-(5-Azacytosin-1-yl-methyl)-isosorbide 5.2 g of 5-0-(5-azacytosin-1-yl-methyl)-2-0-(4-toluyl)-isosorbide was dissolved in 100 ml methanol, and 5 ml of 30% sodium methylate solution was added. The mixture was stirred at room temperature until a thin layer chromatogram indicated complete transesterification, neutralized by addition of 50 ml of ion exchanger Amberlite IR-120 (H+, methanol-washed) and filtered, and the filtrate was evaporated to dryness in vacuo. The residue was recrystallized from ethanol.

Yield: 1.8 g; m.p. 160°–162° C.; $[a]D^{20}+60$ (c=1, water). $C_{10}H_{14}N_4O_5$ MW 270.25

EXAMPLE 28

5-0-(Uracil-1-yl-methyl)-isosorbide

A. 2-0-Benzyl-5-0-chloromethyl-isosorbide

A suspension of 56.9 g of 2-0-benzyl-isosorbide and 15.6 g paraformaldehyde in 120 ml methylene chloride was cooled to 0° C. and saturated with hydrogen chloride at this temperature. The resulting solution was left at 0° to 2° C. for 15 to 20 hours, the water which separated was removed, the organic phase dried over calcium chloride and magnesium sulfate and filtered, and the filtrate was concentrated in vacuo. The viscous oil which remained was further reacted as crude product.

Yield: 70 g $C_{14}H_{17}ClO_4$ MW 284.74

B. 2-0-Benzyl-5-0-(uracil-1-yl-methyl)-isosorbide 25.8 g of 2,4-bis-(trimethylsilyl)-uracil (prepared from uracil analogous to Example 1B) was dissolved in 100 ml dry chloroform, 28.5 g of crude 2-0-benzyl-5-0-chloromethyl-isosorbide was added and the solution stirred at room temperature until reaction was complete (3 hours according to the thin layer chromatogram). All the volatile portions were evaporated in vacuo. The residue was dissolved in 100 ml methylene chloride, the solution stirred with 100 ml of saturated sodium bicarbonate solution until the evolution of gas had ended, the lower layer separated and concentrated in vacuo and the oil which remained was purified by chromatography on silica gel (mobile phase chloroform/methanol (9:1). The pure compound was obtained as a non-crystallizing resin.

Yield: 25.6 g; $[a]D^{20}+58$ (c=2, methylene chloride). $C_{18}H_{20}N_2O_6$ MW 360.38

C. 5-0-(Uracil-1-yl-methyl)-isosorbide 11 g of 2-0-benzyl-5-0-(uracil-1-yl-methyl)-isosorbide was dissolved in 150 ml methanol, 2 g palladium-on-charcoal (5%) was added and the mixture hydrogenated at room temperature under normal pressure. As soon as the uptake of hydrogen had ended, the catalyst was filtered and the filtrate concentrated to dryness in vacuo. The residue was recrystallized from methanol.

Yield: 3.3 g; m.p. 136°–137° C.; $[a]D^{20}+65$ (c=2, water). $C_{11}H_{14}N_2O_6$ MW 270.25

EXAMPLE 29

2-0-(3-Carbamoyl-1,2,4-triazol-1-yl-methyl)-isomannide

A. 2-0-Benzoyl-5-0-chloromethyl-isomannide 175.2 g of 2-0-benzoyl-isomannide and 42.5 g of paraformaldehyde were suspended in 350 ml methylene chloride. Hydrogen chloride was passed in at 0° C. until the suspension was saturated. After the mixture had been left at 0° to 2° C. for 18 to 20 hours, the water of reaction which separated was removed, the mixture was dried over calcium chloride and then magnesium sulfate, and filtered. The filtrate was concentrated in vacuo. A viscous oil which did not crystallize was obtained. The crude compound was further processed in this form.

Yield: 218 g. $C_{14}H_{15}ClO_5$ MW 298.73

B. 2-0-Benzoyl-5-0(3-methoxycarbonyl-1,2,4-triazol-1-yl-methyl)-isomannide and 2-0-benzoyl-5-0-(5-methoxycarbonyl-1,2,4-triazol-1-yl-methyl)-isomannide 20 g of the crude trimethylsilyl compound of methyl 1,2,4-triazole-3-carboxylate (prepared analogous to Example 7A from 12.7 g methyl 1,2,4-triazole-3-carboxylate) and 31 g of crude 2-0-benzoyl-5-0-chloromethyl-isomannide were dissolved in 100 ml dry chloroform and the solution was left at room temperature until complete reaction was shown by the thin layer chromatogram (17 hours). A slight cloudiness was filtered, the filtrate evaporated in vacuo, the syrup dissolved in 100 ml methylene chloride and the solution extracted by stirring with 50 ml of sodium bicarbonate solution for 2 hours and then with 100 ml water, and evaporated in vacuo. The residue was purified by chromatography on silica gel (mobile phase chloroform/methanol 95:5); the two isomers were separated at the same time. 2-0-Benzoyl-5-0-(3-methoxycarbonyl-1,2, 4-triazol-1-yl-methyl)-isomannide was obtained as a solid after recrystallization from ethanol.

Yield: 8.1 g; m.p. 125°–126° C.; $[a]D^{20}+98.5$ (c=2, methylene chloride).

In addition, 2-0-benzoyl-5-0-(5-methoxycarbonyl-1,2,4-triazol-1-yl-methyl)-isomannide was isolated as a viscous oil.

Yield: 12.4 g; $[a]D^{20}+98.5$ (c=2, methylene chloride). $C_{18}H_{19}N_3O_7$ MW 389.38

C. 2-0-(3-Carbamoyl-1,2,4-triazol-1-yl-methyl)-isomannide 7.5 g of 2-0-benzoyl-5-0-(3-methoxycarbonyl-1,2, 4-triazol-1-yl-methyl)-isomannide was suspended in 70 ml of methanol, 7.2 g ammonia was passed in at a maximum temperature of 25° C. under gradual dissolution. The mixture was left at room temperature until the reaction was complete (16 hours according to the thin layer chromatogram) and was concentrated to dryness in vacuo. The solid residue was recrystallized from ethanol.

Yield: 4.1 g; m.p. 135.5°–137.5° C.; $[a]D^{20}+104$ (c=2, water). $C_{10}H_{14}N_4O_5$ MW 270.25

EXAMPLE 30

2-0-(5-Carbamoyl-1,2,4-triazol-1-yl-methyl)-isomannide 11 g of 2-0-benzoyl-5-0-(5-methoxycarbonyl-1,2, 4-triazol-1-yl-methyl)-isomannide (synthesis in Example 29B) was dissolved in 80 ml methanol, and 10.5 g ammonia passed in at a maximum temperature of 25°. The mixture was left at 20°–25° C. for 18–20 hours. A thin layer chromatogram indicated complete reaction. The mixture was concentrated in vacuo and the solid recrystallized from methanol.

Yield: 3.8 g; m.p. 144°–145° C.; $[a]D^{20}+93.5$ (c=2, water). $C_{10}H_{14}N_4O_5$ MW 270.25

EXAMPLE 31

2-0-(5-Iodouracil-1-yl-methyl)-isomannide

A. 2-0-Benzoyl-5-0-(5-iodouracil-1-yl-methyl)isomannide 19.1 g of 2,4-bis-(trimethylsilyl)-5-iodouracil (prepared analogous to Exaple 1B from 5-iodouracil) and 31 g of crude 2-0-benzoyl-5-0-chloromethyl-isomannide (Example 29A) was dissolved in 100 ml dry chloroform and the solution left at room temperature until everything had reacted (after 5 days, in the thin layer chromatogram). The volatile constituents were evaporated in vacuo, the syrup which remained was dissolved in 100 ml methylene chloride and the solution stirred with 50 ml of sodium bicarbonate solution for 2 hours. After the organic layer had been separated and concentrated, a viscous oil was obtained, and purified by chromatography on silica gel (mobile phase chloroform/methanol 9:1). The appropriate fractions were evaporated in vacuo and recrystallized from toluene.

Yield: 10.7 g; m.p. 150°–152° C.; $[a]D^{20}+110.8$ (c=2, methylene chloride). $C_{18}H_{17}IN_2O_7$ MW 500.26

B. 2-0-(5-Iodouracil-1-yl-methyl)-isomannide 9.5 g of 2-0-benzoyl-5-0-(5-iodouracil-1-yl-methyl)-isomannide, suspended in 100 ml methanol, was stirred with 5 ml of 30% sodium methylate solution until solution and complete transesterification (1 hour according to the thin layer chromatogram). The mixture was neutralized by addition of 50 ml of methanol-washed ion exchanger (Amberlite IR-120, H+) and filtered, the filtrate was evaporated in vacuo and the vitreous residue dissolved in hot isopropanol. On cooling, an amorphous precipitate separated and was filtered. The solid was dissolved in water and the solution freezedried.

Yield: 5 g; m.p. 60°–80° C.; $[a]D^{20}+62.5$ (c=2, water). $C_{11}H_{13}IN_2O_6$ MW 396.15

EXAMPLE 32

2-0-(5-Iodouracil-1-yl-methyl)-isoidide

A. 2-0-Benzoyl-5-0-chloromethyl-isoidide 62.5 g of 2-0-benzoyl-isoidide and 15.2 g paraformaldehyde, suspended in 150 ml methylene chloride, were saturated with hydrogen chloride at 0° C. The mixture was left at 0° to 2° C. for 18–20 hours. The water formed was separated, the mixture dried over calcium chloride and magnesium sulfate and filtered. The filtrate was concentrated in vacuo. An oil, which was further reacted in this form, was obtained.

Yield: 70.6 g. $C_{14}H_{15}ClO_5$ MW 298.73

B. 2-0-Benzoyl-5-0-(5-iodouracil-1-yl-methyl)isoidide

A solution of 38.2 g of 2,4-bis-(trimethylsilyl)-5-iodouracil (prepared analogous to Example 1B from 5-iodouracil) and 30 g of crude 2-0-benzoyl-5-0-chloromethyl-isoidide in 100 ml of anhydrous chloroform was stirred at room temperature until a thin layer chromatogram indicated complete reaction (20 hours). All the volatile portions were evaporated in vacuo; the residue was dissolved in 100 ml methylene chloride and the solution extracted by stirring with 50 ml of saturated sodium bicarbonate solution. The organic layer was dried over magnesium sulfate and filtered. The filtrate was concentrated in vacuo and the residue recrystallized from isopropanol.

Yield: 39.1 g; m.p. 80°–85° C.; $[a]D^{20}+33.8$ (c=2, methylene chloride). $C_{18}H_{17}IN_2O_7$ MW 500.26

C. 2-0-(5-Iodouracil-1-yl-methyl)-isoidide 36.7 g of 2-0-benzoyl-5-0-(5-iodouracil-1-yl-methyl)-isoidide was dissolved in 300 ml methanol, and 20 ml sodium methylate was added. The mixture was stirred until, according to the thin layer chromatogram, everything had reacted (15 minutes) and neutralized with 200 ml of Amberlite IR-120 (H+, methanol-washed). The exchanger was filtered, the filtrate concentrated in vacuo and the residue recrystallized from 90% aqueous methanol.

Yield: 17.5 g; m.p. 115°–117° C.; $[\alpha]_D^{20}+22.5$ (c=1, methanol). $C_{11}H_{13}IN_2O_6 \cdot H_2O$ MW 414.17

EXAMPLE 33

2-0-(Carbamoyl-1,2,4-triazol-1-yl-methyl)-isoidide

A.

2-0-Benzoyl-5-0-(3-methoxycarbonyl-1,2,4-triazol-1-yl-methyl)-isoidide and
2-0-benzoyl-5-0-(5-methoxycarbonyl-1,2,4-triazol-1-yl-methyl)-isoidide 20 g of the crude trimethylsilyl compound of methyl 1,2,4-triazole-3-carboxylate (synthesized from 12.7 g of methyl 1,2,4-triazole-3-carboxylate analogous to Example 7A) and 30 g of crude 2-0-benzoyl-5-0-chloromethyl-isoidide (Example 32A) were stirred in 100 ml anhydrous chloroform until complete reaction was detectable in the thin layer chromatogram (20 hours). The mixture was concentrated in vacuo, the residue dissolved in 100 ml methylene chloride, the solution extracted by stirring with 50 ml of saturated sodium bicarbonate solution for 2 hours and the methylene chloride layer separated and evaporated in vacuo. The viscous oil which remained was purified by chromatography on silica gel (mobile phase chloroform/methanol 9:1) and the two isomers were resolved at the same time. 2-0-Benzoyl-5-0-(5-methoxycarbonyl-1,2,4-triazol-1-yl-methyl)-isoidide was obtained as a crystalline product.

Yield: 7.2 g; m.p. 90°–90.5° C.; $[\alpha]_D^{20}+44.8$ (c=2, methylene chloride).

2-0-Benzoyl-5-0-(3-methoxycarbonyl-1,2,4-triazol-1-yl-methyl)-isoidide was also obtained, as an oil.

Yield: 14.3 g; $[\alpha]_D^{20}+17.3$ (c=2, methylene chloride). $C_{18}H_{19}N_3O_7$ MW 389.38

B. 2-0-(3-Carbamoyl-1,2,4-triazol-1-yl-methyl)isoidide

A solution of 14 g of 2-0-benzoyl-5-0-(3-methoxycarbonyl-1,2,4-triazol-1-yl-methyl)-isoidide in 100 ml methanol was saturated with ammonia at a maximum tempeature of 25° C. and the mixture was left at room temperature until a thin layer chromatogram indicated complete reaction (2 days). The volatile constituents were distilled in vacuo until a volume of about 50 ml. The solid which precipitated was filtered with suction and recrystallized from methanol.

Yield: 5.3 g; m.p. 192.5°–193° C.; $[\alpha]_D^{20}+7$ (c=1, water). $C_{10}H_{14}N_4O_5$ MW 270.25

EXAMPLE 34

2-0-(5-Carbamoyl-1,2,4-triazol-1-yl-methyl)isoidide 7 g of 2-0-benzoyl-5-0-(5-methoxycarbonyl-1,2,4-triazol-1-yl-methyl)-isoidide was suspended in 50 ml methanol, and ammonia passed in at a maximum temperature of 25° C. until the suspension was saturated. After 2 days, everything had reacted according to the thin layer chromatogram. The mixture was concentrated and the residue purified by chromatography on silica gel (mobile phase chloroform/methanol 4:1). The appropriate fractions were concentrated and the crude product was recrystallized from ethanol.

Yield: 3.1 g; m.p. 126°–126.5° C.; $[\alpha]_D^{20}+16.5$ (c=2, water). $C_{10}H_{14}N_4O_5$ MW 270.25

EXAMPLE 35

2-0-(5-Methyluracil-1-yl-methyl)-isosorbide-5-monophosphoric acid 11 g of 2-0-(5-methyluracil-1-yl-methyl)-isosorbide (Example 5) was suspended in 40 ml acetonitrile, 11 ml phosphorus oxytrichloride was added and the mixture cooled to 5°–10° C. A solution of 3 ml pyridine in 10 ml acetonitrile was then added at a maximum temperature of 10° C. and the mixture allowed to warm slowly to room temperature. Dissolution occurred at 17°–18° C. As soon as a thin layer chromatogram indicated complete reaction (30 minutes), the reaction mixture was poured onto 1 L of ice-water, 110 g of active charcoal (Carboraffin P) was added and the mixture stirred until, according to the thin layer chromatogram, all the UV-absorbing constituents had bonded to the charcoal. The active charcoal was filtered with suction and washed with water until free from chloride and phosphate. Elution was then carried out with a total of 2–3 L of 3% aqueous-methanolic ammonia (water/methanol 9:1), until a sample of the eluate no longer showed UV absorption. The combined eluates were concentrated in vacuo, the syrup which remained was dissolved in 90% aqueous methanol and the product precipitated with ethanol. The pure title compound was obtained as a crystalline diammonium salt.

Yield: 7 g; m.p. decomp.>110° ; $[\alpha]_D^{20}+29$ (c=1, water). $C_{12}H_{23}N_4O_9P$ MW 398.32

EXAMPLE 36

2-0-(4-Hydroxy-1H-pyridin-2-on-1-yl-methyl)-isosorbide

A.

2-0-(4-Hydroxy-1H-pyridin-2-on-1-yl-methyl)-5-0-(4-toluyl)-isosorbide 12.8 g of 2,4-bis=(trimethylsilyloxy)-pyridine (prepared from 4-hydroxy-2-pyridone and hexamethyldisilazane analogous to Example 1B) and 16.5 g of crude 2-0-chloromethyl-5-0-(4-toluyl)-isosorbide (Example 1A) were dissolved in 100 ml dry chloroform. The solution was stirred at room temperature until a thin layer chromatogram indicated complete reaction (4 hours). The mixture was concentrated in vacuo, the residue dissolved in methanol, the solution concentrated again, the crude product purified by chromatography on silica gel (mobile phase chloroform/methanol 9:1) and the product recrystallized from ethyl acetate.

Yield: 10.5 g; m.p. 100°–101° C. (decomp.); $[\alpha]_D^{20}+48.5$ (c=1, methanol). $C_{20}H_{21}NO_7$ MW 387.40

B.

2-0-(4-Hydroxy-1H-pyridin-2-on-1-yl-methyl)-isosorbide 6.7 g of 2-0-(4-hydroxy-1H-pyridin-2-on-1-yl-methyl)-5-0-(4-toluyl)-isosorbide and 4 ml of 30% sodium methylate solution were dissolved in 50 ml methanol. The solution was stirred until transesterification was complete (1 hour according to the thin layer chromatogram). The mixture was neutralized by addition of 40 ml of methanol-washed Amberlite IR-120 (H+), exchanger was filtered with suction and the filtrate concentrated to dryness in vacuo. The residue was recrystallized form ethanol.

Yield: 2.8 g; m.p. 178°–179° C.; $[\alpha]_D^{20}+43.5$ (c=1, water). $C_{12}H_{15}NO_6$ MW 269.26

EXAMPLE 37

5-0-(5-Methyluracil-1-yl-methyl)-isosorbide

A. 5-0-(5-Methyluracil-1-yl-methyl)-2-0-(4-toluyl)isosorbide

13.6 g of 2,4-bis-(trimethylsilyl)-5-methyluracil (preparation from 5-methyluracil analogous to Example 1B) was dissolved in 50 ml dry chloroform, and 16.3 g of crude 5-0-chloromethyl-2-0-(4-toluyl)-isosorbide (Example 24, method 1B) was added. The mixture was stirred until complete reaction according to the thin layer chromatogram (4 hours). The mixture was concentrated to a syrup in vacuo, the syrup dissolved in 50 ml methylene chloride and the solution stirred with 20 ml of saturated sodium bicarbonate solution until the evolution of gas had ended. The organic phase was separated and concentrated in vacuo. The residue was dissolved in methanol and the solution evaporated again. 19 g of crude product, which was further processed without purification, was obtained. $C_{20}H_{22}N_2O_7$ MW 402.41

B. 5-0-(5-Methyluracil-1-yl-methyl)-isosorbide

19 g of crude 5-0-(5-methyluracil-1-yl-methyl)-2-0-(4-toluyl)-isosorbide was dissolved in 50 ml of methanol, and 5 ml of 30% sodium methylate solution added. The mixture was stirred until a thin layer chromatogram indicated complete reaction (1.5 hours) and was neutralized by addition of 50 ml of ion exchanger (Amberlite IR-120, H+, methanol-washed) and filtered. The filtrate was concentrated in vacuo. The oily residue was purified by chromatography on silica gel (mobile phase chloroform/methanol 9:1). Concentration of the corresponding fractions gave a vitreous product which was dissolved in water and freeze-dried.

Yield: 2.6 g; m.p. 48°-55° C.; $[a]D^{20}+69.5$ (c=1, water). $C_{12}H_{16}N_2O_6 \cdot 0.5\ H_2O$ MW 293.28

EXAMPLE 38

2-0-(5-Methyluracil-1-yl-methyl)-isomannide 11.3 g of 2,4-bis-(trimethylsilyl)-5-methyluracil (prepared analogous to Example 1B from 5-methyluracl) and 13.3 g of crude 2-0-benzoyl-5-0-chloromethyl-isomannide (Example 29A) were stirred in 50 ml chloroform until complete reaction according to a thin layer chromatogram (17 hours). After concentrating the mixture in vacuo and dissolving the residue in 50 ml methylene chloride, the solution was extracted by stirring with 20 ml of saturated sodium bicarbonate solution for one hour. The organic phase was separated and concentrated in vacuo. The residue was dissolved in methanol, the solution concentrated again and the residue of crude 2-0-benzoyl-5-0-(5-methyluracil-1-yl-methyl)-isomannide taken up in 50 ml methanol.

8 ml of 30% sodium methylate solution was added, the mixture stirred until a thin layer chromatogram demonstrated complete transesterification, the mixture neutralized with 80 ml of Amberlite IR-120 (H+, methanol-moist) and the exchanger filtered with suction. The filtrate was concentrated in vacuo and the vitreous crude product purified by chromatography on silica gel (mobile phase chloroform/methanol 9:2). Recrystallization from ethyl acetate gave the pure title compound.

Yield: 4.5 g; m.p. 141°-142° C.; $[a]D^{20}+92$ (c=1, water). $C_{12}H_{16}N_2O_6$ MW 284.27

EXAMPLE 39

2-0-(5-Methyluracil-1-yl-methyl)-isoidide 8.5 g of 2,4-bis-(trimethylsilyl)-5-methyluracil (preparation analogous to Example 1B from 5-methyluracil) and 9.1 g of crude 2-0-benzoyl-5-0-chloromethyl-isoidide dissolved in 50 ml of dry chloroform were stirred at room temperature until a thin layer chromatogram indicated complete reaction (15 hours). The mixture was concentrated in vacuo, the residue dissolved in 50 ml methylene chloride, the solution stirred with 20 ml of sodium bicarbonate solution until the evolution of gas had ended, the organic layer separated and concentrated in vacuo, the residue subsequently evaporated with methanol and the crude 2-0-benzoyl-5-0-(5-methyluracil-1-yl-methyl)-isoidide dissolved in 100 ml methanol.

After addition of 6 ml of 30% sodium methylate solution, the mixture was stirred until complete transesterification according to the thin layer chromatogram (30 minutes). The product formed was neutralized by stirring with 60 ml of Amberlite IR-120 (H+, methanol-washed) and filtered. The filtrate was concentrated in vacuo. The residue was recrystallized from ethyl acetate.

Yield: 5.3 g; m.p. 163°-165° C.; $[a]D^{20}+16$ (c=1, water). $C_{12}H_{16}N_2O_6$ MW 284.27

We claim:

1. An isohexide nucleoside of formula I:

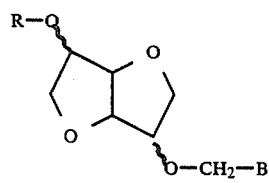

or a pharmaceutically accceptable acid-addition salt thereof; wherein the bond between the ring system and the substituents can be either endocyclic or exocyclic; R is hydrogen; straight-chain or branched aliphatic acyl with 2 to 5 carbon atoms; benzyl or toluyl each optionally substituted by halogen, lower alkyl or nitro; benzyl; or phosphate, and B is a heterocyclic group selected from the group consisting of (a) a uracil of the formula II:

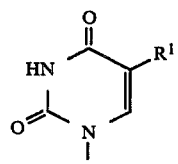

wherein $R^1$ is hydrogen; halogen; or alkyl, alkenyl or alkynyl having 1 to 6 carbon atoms, each optionally substituted by hydroxyl or halogen, (b) a cytosine of the formula III:

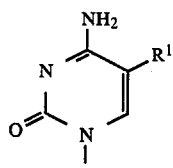

in which R¹ has the abovementioned meaning,
(c) an isocytosine of the formula IV:

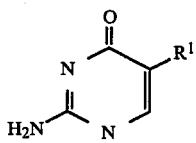

in which R¹ has the abovementioned meaning,
(d) a 5-azacytosine of hte formula V:

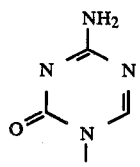

(e) a triazole of the formula VI:

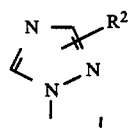

in which R² occupies either the 3- or the 5-position and has the following meaning:
hydrogen, alkoxycarbonyl COOR³, in which R³ is alkyl with 1 to 5 carbon atoms, carboxamide, thiocarboxamide or cyano, or
(f) an imidazole of the formula VII:

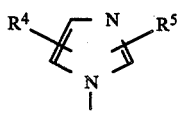

in which R⁴ and R⁵ are identical or different and are hydrogen, amino, carboxamide, thiocarboxamide or cyano; or a pharamaceutically acceptable acid addition salt thereof.

2. A compound according to claim 1, which is an isomannide compound of formula Ia:

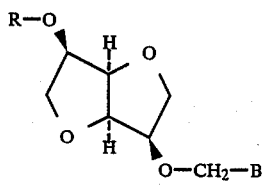

in which R and B are as defined in claim 1.

3. A compound according to claim 1, which is an isoidide compound of formula Ib:

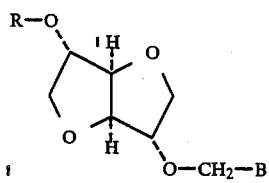

in which R and B are as defined in claim 1.

4. A compund according to claim 1, which is an isosorbide compound of formula Ic or Id:

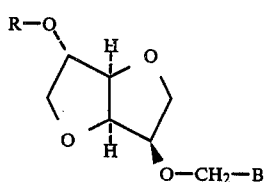

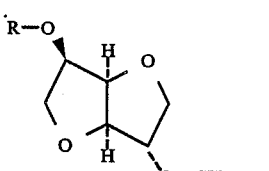

in which R and B are as defined in claim 1.

5. A compound according to claim 1, in which R is hydrogen or phosphate.

6. A compound according to claim 1, in which R is hydrogen or phosphate, B is as defined in claim 18, R¹ is hydrogen, methyl, ethyl, propyl, isopropyl, butyl, isobutyl, pentyl, hexyl, hydroxymethyl, hydroxyethyl, vinyl, allyl, ethynyl, fluorine, chlorine, bromine, iodine, bromoyvinyl, iodovinyl or trifluoromehtyl, R² is carboxamide, methoxycarbonyl or ethoxycarbonyl, and one of R⁴ and R⁵ is amino and the other carboxamide or cyano.

7. A pharmaceutical composition comprising a cytostatic or immunostimulating effective amount of a compound of formula I as defined in claim 1 and a pharmaceutically acceptable carrier.

8. A method for achieving cytostatic effect in a subject in need of such treatment which comprises administering to a subject in need of such treatment a compound of formula I as defined in claim 1 in an amount sufficient for achieving such effect.

9. An isohexide nucleoside of formula I:

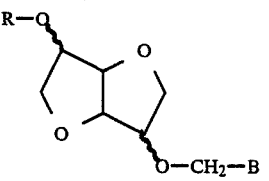

or a pharmaceutically acceptable acid-addition sa wherein the bond between the ring system and the substituents can be either endocyclic or exocyclic; R is hydrogen; straight-chain or branched aliphatic acyl with 2 to 5 carbon atoms; benzoyl or toluyl each optionally substituted by halogen, lower alkyl or nitro; benzyl;

or phosophate, and B is a heterocyclic group selected from the group consisting of:

(a) a uracil of the formula II:

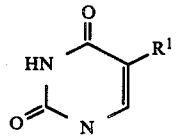

(b) a cytosineof the formula III:

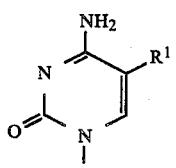

(c) an isocytosine of the formula IV:

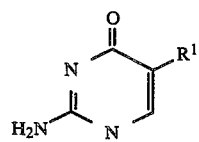

wherein R¹ in formula II, III and IV is hydrogen; halogen; or alkyl, alkenyl or alkynyl having 1 to 6 carbon atoms, each optionally substituted by hydroxyl or halogen, and the pharmaceutically acceptable acid addition salts of the foregoing heterocyclic groups.

10. A compound according to claim 9, which is an isomannide compound of formula Ia:

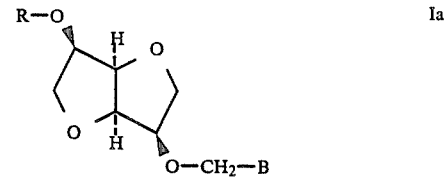

in which R and B are as defined in claim 9.

11. A compound according to claim 9, which is an isodide compound of formula Ib:

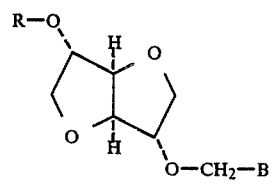

in which R and B are as defined in claim 9.

12. A compound according to claim 9, which is an isosorbide compound of formula Ic or Id:

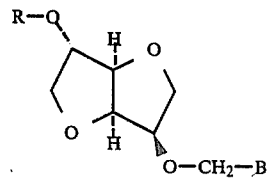

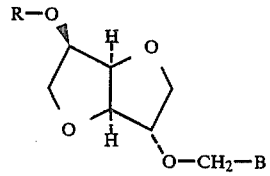

in which R and B are as defined in claim 9.

13. A compound according to claim 9, in which R is hydrogen or phosphate.

14. A pharmaceutical composition comprising an antiviral, cytostatic or immunostimulating effective amount of a compound of formula I as defined in claim 9 and a pharmaceutically acceptable carrier.

15. A method for the prevention or treatment of susceptible viral disease which comprises administering to a subject in need of such treatment a compound of formula I as defined in claim 9 in an amount sufficient for the prevention or treatment of such viral disease.

* * * * *